(12) United States Patent
Hanaoka et al.

(10) Patent No.: US 8,026,324 B2
(45) Date of Patent: Sep. 27, 2011

(54) TRANSITION METAL COMPLEX, PROCESS FOR PRODUCING THE SAME, AND USE

(75) Inventors: Hidenori Hanaoka, Suita (JP); Masaaki Nabika, Ichihara (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/531,852

(22) PCT Filed: Mar. 18, 2008

(86) PCT No.: PCT/JP2008/054967
§ 371 (c)(1),
(2), (4) Date: Sep. 17, 2009

(87) PCT Pub. No.: WO2008/114790
PCT Pub. Date: Sep. 25, 2008

(65) Prior Publication Data
US 2010/0063228 A1    Mar. 11, 2010

(30) Foreign Application Priority Data
Mar. 20, 2007  (JP) .................. 2007-072128

(51) Int. Cl.
C08F 4/642    (2006.01)
C08F 4/6592   (2006.01)
C07F 17/00    (2006.01)
B01J 31/22    (2006.01)

(52) U.S. Cl. ........ 526/160; 526/133; 526/134; 526/165; 526/348; 502/103; 502/152; 556/53

(58) Field of Classification Search .......... 556/53; 526/133, 134, 160, 165, 348; 502/103, 152
See application file for complete search history.

(56) References Cited

U.S. PATENT DOCUMENTS
5,807,936 A       9/1998  Fritze et al.
2005/0197471 A1*  9/2005  Fujita et al. .................. 526/177

FOREIGN PATENT DOCUMENTS
EP  0842939 A1   5/1998
EP  0 955 304 A2 11/1999
EP  1498178 A2   1/2005
WO  97/03992 A1   2/1997
WO  98/16311 A1   4/1998
WO  03/045963 A1  6/2003

OTHER PUBLICATIONS

H. Hanaoka et al., "Synthesis and characterization of titanium alkyl, oxo, and diene complexes bearing a SiMe$_2$-bridged phenoxy-cyclopentadienyl ligand and their catalytic performance for copolymerization of ethylene and 1-hexene", Journal of Organometallic Chemistry, vol. 692, 2007, pp. 4717-4724.

* cited by examiner

Primary Examiner — Caixia Lu
(74) Attorney, Agent, or Firm — Sughrue Mion, PLLC

(57) ABSTRACT

A transition metal complex of the following formula (1):

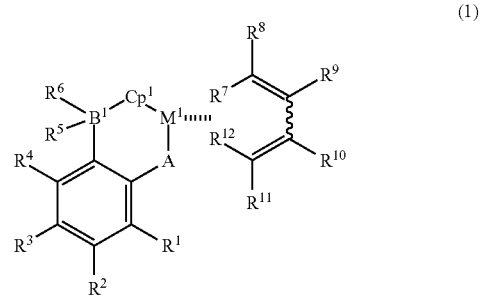

in which A represents an atom of Group 16 of the periodic table; $B^1$ represents an atom of Group 14 of the periodic table; $M^1$ represents a transition metal atom of Group 4 of the periodic table; $Cp^1$ represents a group having a cyclopentadiene anion backbone; $R^1$, $R^2$, $R^3$, $R^4$, $R^5$ and $R^6$ represent independently of one another a hydrogen atom, a halogen atom, a $C_{1-20}$ alkyl group optionally substituted with a halogen atom; $R^7$, $R^8$, $R^9$, $R^{10}$, $R^{11}$ and $R^{12}$ represent independently of one another a hydrogen atom, a $C_{1-20}$ alkyl group optionally substituted with a halogen atom; and a 1,3-diene comprising $R^7$, $R^8$, $R^9$, $R^{10}$, $R^{11}$, $R^{12}$ and 4 carbon atoms coordinates on $M^1$, and the 1,3-diene may be of either a cis or trans form, or a mixed form thereof, although the coordination form is not limited, and the double bonds may be delocalized. When this transition metal complex is used as a catalytic component, high molecular weight polyolefin is produced with high catalytic activity.

13 Claims, No Drawings

TRANSITION METAL COMPLEX, PROCESS FOR PRODUCING THE SAME, AND USE

FIELD OF THE INVENTION

The present invention relates to transition metal complexes, and production processes and usage thereof.

BACKGROUND ART

Hitherto, many processes have been developed for producing olefin polymers using metallocene complexes (e.g., JP-A-58-19309). It is reported that a complex having a ligand which comprises a phenoxy group and a cyclopentadienyl group crosslinked with each other through a bonding group, for example, dimethylsilyl(tetramethyl-cyclopentadienyl)(3-tert-butyl-5-methyl-2-phenoxy)titanium dichloride, is activated by a co-catalyst to show high catalytic activity for polymerizing an α-olefin, so that high molecular weight polyolefin can be produced (cf. JP-A-9-87313 and JP-A-2003-176295). However, there is a demand for an olefin polymerization catalyst capable of providing a high molecular weight polyolefin with still higher polymerization activity.

DISCLOSURE OF THE INVENTION

Problems to be Solved by the Invention

An object of the present invention is to provide a novel transition metal complex with a higher activity, having a ligand which comprises an aryl group modified with an atom of Group 16 of the periodic table and a cyclopentadienyl group crosslinked with each other by a bonding group.

Means for Solving the Problems

As a result of the present inventors' intensive studies on a novel transition metal complex so as to solve the above-described problem, a novel transition metal complex having a 1,3-diene as a ligand has been discovered.

Accordingly, the present invention provides a transition metal complex of the formula (1), a catalyst containing the transition metal complex for use in the polymerization of an olefin, and a process for producing an olefin polymer using this catalyst:

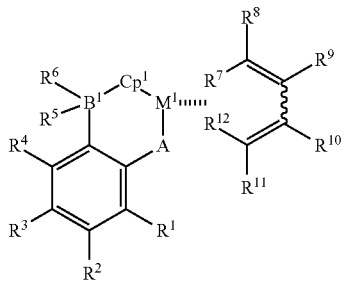
(1)

wherein A represents an atom of Group 16 of the periodic table;
$B^1$ represents an atom of Group 14 of the periodic table;
$M^1$ represents a transition metal atom of Group 4 of the periodic table;
$Cp^1$ represents a group having a cyclopentadiene anion backbone;

$R^1$, $R^2$, $R^3$, $R^4$, $R^5$ and $R^6$ represent independently of one another a hydrogen atom, a halogen atom, a $C_1$-$C_{20}$ alkyl group optionally substituted with a halogen atom, a $C_7$-$C_{20}$ aralkyl group optionally substituted with a halogen atom, a $C_6$-$C_{20}$ aryl group optionally substituted with a halogen atom, a $C_1$-$C_{20}$ hydrocarbon-substituted silyl group in which the hydrocarbon is optionally substituted with a halogen atom, a $C_1$-$C_{20}$ alkoxy group optionally substituted with a halogen atom, a $C_7$-$C_{20}$ aralkyloxy group optionally substituted with a halogen atom, a $C_6$-$C_{20}$ aryloxy group optionally substituted with a halogen atom, or a $C_2$-$C_{20}$ hydrocarbon-disubstituted amino group;

$R^7$, $R^8$, $R^9$, $R^{10}$, $R^{11}$ and $R^{12}$ represent independently of one another a hydrogen atom, a $C_1$-$C_{20}$ alkyl group optionally substituted with a halogen atom, a $C_7$-$C_{20}$ aralkyl group optionally substituted with a halogen atom, or a $C_6$-$C_{20}$ aryl group optionally substituted with a halogen atom, with the proviso that adjacent groups among $R^1$, $R^2$, $R^3$, $R^4$, $R^5$, $R^6$, $R^7$, $R^8$, $R^9$, $R^{10}$, $R^{11}$ and $R^{12}$ may be optionally bonded to each other to form a ring; and that a 1,3-diene consisting of $R^7$, $R^8$, $R^9$, $R^{10}$, $R^{11}$, $R^{12}$ and 4 carbon atoms coordinates on $M^1$ without any limitation of its coordination form, and the 1,3-diene may be of either a cis or trans form, or a mixed form thereof, and the double bonds may be delocalized.

Effect of the Invention

According to the present invention, the use of the transition metal complex of the formula (1) as a catalytic component makes it possible to produce high molecular weight polyolefin with high catalytic activity.

DETAILED DESCRIPTION OF THE INVENTION

Hereinafter, the present invention will be described in detail.

[Transition Metal Complex (1)]

In the transition metal complex of the formula (1) (hereinafter referred to as the transition metal complex (1)), the coordination form of the 1,3-diene to $M^1$ is not particularly limited. That is, the 1,3-diene may be of either a cis or trans form, or a mixed form thereof, and the double bonds may be delocalized. The coordination form of the 1,3-diene may be, for example, of a η4 type (1-A; s-cis, 1-B; s-trans), or of a σ2π type (1-C), depending on its electron state, or of a mixed form thereof, and the electron localized state may be in between the η4 form and the σ2π form.

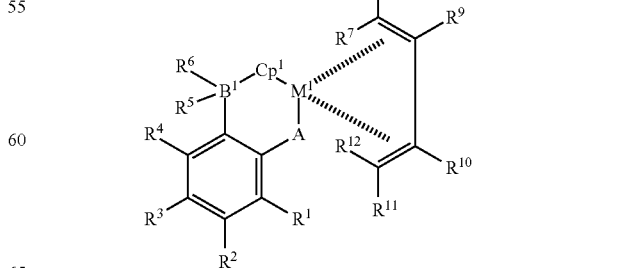
(1-A)

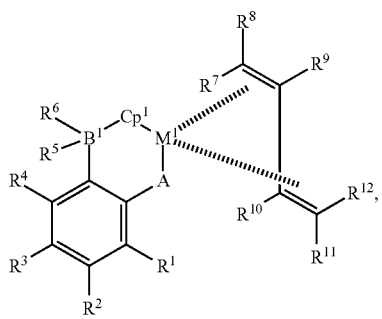

(1-B)

(1-C)

The structure (1-A) of the 1,3-diene can be classified to 1-A-a and 1-A-b depending on its steric structure, and may be of either 1-A-a or 1-A-b, or of a mixed form thereof.

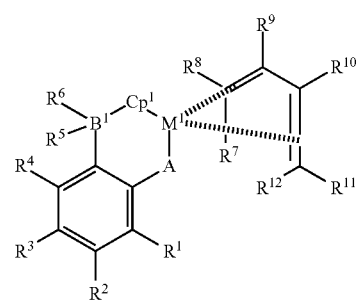

(1-A-a)

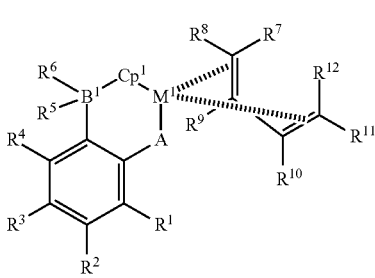

(1-A-b)

Examples of the alkyl group having 1 to 20 carbon atoms for $R^1, R^2, R^3, R^4, R^5, R^6, R^7, R^8, R^9, R^{10}, R^{11}$ and $R^{12}$ include a methyl group, an ethyl group, a n-propyl group, an isopropyl group, a n-butyl group, a sec-butyl group, a tert-butyl group, a n-pentyl group, a neopentyl group, an amyl group, a n-hexyl group, a n-octyl group, a decyl group, a n-dodecyl group, a n-pentadecyl group and a n-eicosyl group. Among them, a methyl group, an ethyl group, an isopropyl group, a tert-butyl group and an amyl group are preferable.

Each of these alkyl groups may be substituted with a halogen atom such as a fluorine atom, a chlorine atom, a bromine atom and an iodine atom. Examples of the halogen-substituted alkyl group having 1 to 20 carbon atoms include a fluoromethyl group, a difluoromethyl group, a trifluoromethyl group, a chloromethyl group, a dichloro-methyl group, a trichloromethyl group, a bromomethyl group, a dibromomethyl group, a tribromomethyl group, an iodomethyl group, a diiodomethyl group, a triiodomethyl group, a fluoroethyl group, a difluoroethyl group, a trifluoroethyl group, a tetrafluoroethyl group, a pentafluoroethyl group, a chloroethyl group, a dichloroethyl group, a trichloroethyl group, a tetrachloroethyl group, a pentachloroethyl group, a bromoethyl group, a dibromoethyl group, a tribromoethyl group, a tetrabromoethyl group, a pentabromoethyl group, a perfluoropropyl group, a perfluorobutyl group, a perfluoropentyl group, a perfluorohexyl group, a perfluorooctyl group, a perfluorododecyl group, a perfluoropentadecyl group, a perfluoroeicosyl group, a perchloropropyl group, a perchlorobutyl group, a perchloropentyl group, a perchlorohexyl group, a perchlorooctyl group, a perchlorododecyl group, a perchloropentadecyl group, a perchloroeicosyl group, a perbromopropyl group, a perbromobutyl group, a perbromopentyl group, a perbromohexyl group, a perbromooctyl group, a perbromododecyl group, a perbromopentadecyl group and a perbromoeicosyl group.

Examples of the aralkyl group having 7 to 20 carbon atoms for $R^1, R^2, R^3, R^4, R^5, R^6, R^7, R^8, R^9, R^{10}, R^{11}$ and $R^{12}$ include a benzyl group, a (2-methylphenyl)methyl group, a (3-methylphenyl)methyl group, a (4-methylphenyl)-methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (4,6-dimethylphenyl)methyl group, a (2,3,4-trimethylphenyl)methyl group, a (2,3,5-trimethylphenyl) methyl group, a (2,3,6-trimethylphenyl)-methyl group, a (3,4,5-trimethylphenyl)methyl group, a (2,4,6-trimethylphenyl)methyl group, a (2,3,4,5-tetramethylphenyl)methyl group, a (2,3,4,6-tetramethyl-phenyl)methyl group, a (2,3,5,6-tetramethylphenyl)methyl group, a (pentamethylphenyl) methyl group, an (ethylphenyl)-methyl group, a (n-propylphenyl)methyl group, an (isopropylphenyl)methyl group, a (n-butylphenyl)methyl group, a (sec-butylphenyl)methyl group, a (tert-butylphenyl)methyl group, a (n-pentylphenyl) methyl group, a (neopentylphenyl)methyl group, a (n-hexylphenyl)methyl group, a (n-octylphenyl)methyl group, a (n-decylphenyl)-methyl group, a (n-decylphenyl)methyl group, a (n-tetradecylphenyl)methyl group; a naphthylmethyl group, and an anthracenylmethyl group. Among them, a benzyl group is preferable.

Each of the aralkyl groups may be substituted with a halogen atom such as a fluorine atom, a chlorine atom, bromine atom and an iodine atom.

Examples of the aryl group having 6 to 20 carbon atoms for $R^1, R^2, R^3, R^4, R^5, R^6, R^7, R^8, R^9, R^{10}, R^{11}$ and $R^{12}$ include a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethyl-phenyl group, a 2,3,5,6-tetramethylphenyl group, a pentamethylphenyl group, an ethylphenyl group, a n-propylphenyl group, an isopropylphenyl group, a n-butylphenyl group, a sec-butylphenyl group, a tert-butylphenyl group, a n-pentylphenyl group, a neopentylphenyl group, a n-hexylphenyl group, a n-octylphenyl group, a n-decylphenyl group, a n-dodecylphenyl group, a n-tetradecylphenyl group, a naphthyl group and an anthracenyl group. Among them, a phenyl group is preferable.

Each of the aryl group may be substituted with a halogen atom such as a fluorine atom, a chlorine atom, a bromine atom and an iodine atom.

The hydrocarbon-substituted silyl group for $R^1$, $R^2$, $R^3$, $R^4$, $R^5$ and $R^6$ is a silyl group which is substituted with a hydrocarbon group. Examples of the hydrocarbon group include an alkyl group having 1 to 10 carbon atoms such as a methyl group, an ethyl group, a n-propyl group, an isopropyl group, a n-butyl group, a sec-butyl group, a tert-butyl group, an isobutyl group, a n-pentyl group, a n-hexyl group and a cyclohexyl; and an aryl group such as a phenyl group. Examples of the $C_1$-$C_{20}$-hydrocarbon substituted silyl group include mono-$C_1$-$C_{20}$-hydrocarbon substituted silyl group such as a methylsilyl group, an ethylsilyl group and a phenylsilyl group; di-$C_1$-$C_{20}$-hydrocarbon substituted silyl group such as a dimethylsilyl group, a diethylsilyl group and a diphenylsilyl group; and tri-$C_1$-$C_{20}$-hydrocarbon substituted silyl group silyl group such as a trimethylsilyl group, a triethylsilyl group, a tri-n-propylsilyl group, a triisopropylsilyl group, a tri-n-butylsilyl group, a tri-sec-butylsilyl group, a tri-tert-butylsilyl group, a tri-isobutylsilyl group, a tert-butyl-dimethylsilyl group, a tri-n-pentylsilyl group, a tri-n-hexylsilyl group, a tricyclohexylsilyl group and a triphenylsilyl group. Among them, a trimethylsilyl group, a tert-butyldimethylsilyl group and a triphenylsilyl group are preferable.

The hydrocarbon group(s) of each of the hydrocarbon-substituted silyl groups may be substituted with a halogen atom such as a fluorine atom, a chlorine atom, a bromine atom and an iodine atom.

Examples of the alkoxy groups having 1 to 20 carbon atoms for $R^1$, $R^2$, $R^3$, $R^4$, $R^5$ and $R^6$ include a methoxy group, an ethoxy group, a n-propoxy group, an isopropoxy group, a n-butoxy group, a sec-butoxy group, a tert-butoxy group, a n-pentoxy group, a neopentoxy group, a n-hexyloxy group, a n-octyloxy group, a n-dodecyloxy group, a n-pentadecyloxy group and a n-eicosocyloxy group. Among them a methoxy group, an ethoxy group and a tert-butoxy group are preferable.

Each of the alkoxy groups may be substituted with a halogen atom such as a fluorine atom, a chlorine atom, a bromine atom and an iodine atom.

Examples of the aralkyloxy group having 7 to 20 carbon atoms for $R^1$, $R^2$, $R^3$, $R^4$, $R^5$ and $R^6$ include a benzyloxy group, a (2-methylphenyl)methoxy group, a (3-methylphenyl)methoxy group, a (4-methylphenyl)methoxy group, a (2,3-dimethyl-phenyl)methoxy group, a (2,4-dimethylphenyl)methoxy group, a (2,5-dimethylphenyl)methoxy group, a (2,6-dimethyl-phenyl)methoxy group, a (3,4-dimethylphenyl)methoxy group, a (3,5-dimethylphenyl)methoxy group, a (2,3,4-trimethyl-phenyl)methoxy group, a (2,3,5-trimethylphenyl)methoxy group, a (2,3,6-trimethylphenyl)methoxy group, a (2,4,5-trimethylphenyl)methoxy group, a (2,4,6-trimethyl-phenyl)methoxy group, a (3,4,5-trimethylphenyl) methoxy group, a (2,3,4,5-tetramethylphenyl)methoxy group, a (2,3,4,6-tetramethylphenyl)methoxy group, a (2,3,5,6-tetramethylphenyl)methoxy group, a (pentamethylphenyl)-methoxy group, an (ethylphenyl)methoxy group, a (n-propylphenyl)methoxy group, an (isopropylphenyl)methoxy group, a (n-butylphenyl)methoxy group, a (sec-butylphenyl)methoxy group, a (tert-butylphenyl)methoxy group, a (n-hexylphenyl)methoxy group, a (n-octylphenyl)methoxy group, a (n-decylphenyl)methoxy group, a (n-tetradecyl-phenyl)methoxy group, a naphthylmethoxy group and an anthracenylmethoxy group. Among them, a benzyloxy group is preferable.

Each of the aralkyloxy groups may be substituted with a halogen atom such as a fluorine atom, a chlorine atom, a bromine atom and an iodine atom.

Examples of the aryloxy group for $R^1$, $R^2$, $R^3$, $R^4$, $R^5$ and $R^6$ include aryloxy groups having 6 to 20 carbon atoms such as a phenoxy group, a 2-methylphenoxy group, a 3-methylphenoxy group, a 4-methylphenoxy group, a 2,3-dimethylphenoxy group, a 2,4-dimethylphenoxy group, a 2,5-dimethylphenoxy group, a 2,6-dimethylphenoxy group, a 3,4-dimethylphenoxy group, a 3,5-dimethylphenoxy group, a 2,3,4-trimethylphenoxy group, a 2,3,5-trimethylphenoxy group, a 2,3,6-trimethylphenoxy group, a 2,4,5-trimethylphenoxy group, a 2,4,6-trimethylphenoxy group, a 3,4,5-trimethylphenoxy group, a 2,3,4,5-tetramethylphenoxy group, a 2,3,4,6-tetramethylphenoxy group, a 2,3,5,6-tetramethylphenoxy group, a pentamethylphenoxy group, an ethylphenoxy group, a n-propylphenoxy group, an isopropylphenoxy group, a n-butylphenoxy group, a sec-butylphenoxy group, a tert-butylphenoxy group, a n-hexylphenoxy group, a n-octylphenoxy group, a n-decylphenoxy group, a n-tetradecylphenoxy group, a naphthoxy group and an anthracenoxy group.

Each of the aryloxy groups may be substituted with a halogen atom such as a fluorine atom, a chlorine atom, a bromine atom and an iodine atom.

The di-$C_2$-$C_{20}$-hydrocarbon-substituted amino group means an amino group which is substituted with two hydrocarbon groups. Examples of the hydrocarbon groups include an alkyl group having 1 to 20 carbon atoms such as a methyl group, an ethyl group, a n-propyl group, an isopropyl group, a n-butyl group, a sec-butyl group, a tert-butyl group, an isobutyl group, a n-pentyl group, a n-hexyl group and a cyclohexyl group; and an aryl group such as a phenyl group. Examples of the di-$C_1$-$C_{10}$-hydrocarbon-substituted amino groups include a dimethylamino group, a diethylamino group, a di-n-propylamino group, a diisopropylamino group, a di-n-butylamino group, a di-sec-butylamino group, a di-tert-butylamino group, a diisobutylamino group, a tert-butyl-isopropylamino group, a di-n-hexylamino group, a di-n-octylamino group, a di-n-decylamino group, a diphenylamino group, a bistrimethylsilylamino group and a bis-tert-butyldimethylsilylamino group. Among them, a dimethylamino group and a diethylamino group are preferable.

The adjacent groups among $R^1$, $R^2$, $R^3$, $R^4$, $R^5$, $R^6$, $R^8$, $R^9$, $R^{10}$, $R^{11}$ and $R^{12}$ may be optionally bonded to each other to form a ring.

Each of the substituents $X^1$ and $X^2$ is a halogen atom, preferably a chlorine atom or a bromine atom.

Examples of the atom of Group 16 of the periodic table, represented by A, include an oxygen atom, a sulfur atom and a selenium atom. Among them, an oxygen atom is preferable.

Examples of the atom of Group 14 of the periodic table, represented by B, include a carbon atom, a silicon atom and a germanium atom. Among them, a carbon atom and a silicon atom are preferable.

The transition metal atom represented by $M^1$ is a transition metal atom of Group 4 of the periodic table (IUPAC Nomenclature of Inorganic Chemistry, Revised Edition, 1989), and examples thereof include a titanium atom, a zirconium atom and a hafnium atom.

Examples of a group having a cyclopentadiene anion backbone represented by $Cp^1$ include a η5-cyclopenta-dienyl group, a η5-methylcyclopentadienyl group, a η5-dimethylcyclopentadienyl group, a η5-trimethylcyclopenta-dienyl group, a η5-tetramethylcyclopentadienyl group, a η5-ethylcyclopentadienyl group, a η5-n-propyl-cyclopentadienyl group, a η5-isopropylcyclopentadienyl group, a η5-n-butylcyclopentadienyl group, a η5-sec-butylcyclopentadienyl group, a η5-tert-butylcyclopentadienyl group, a η5-n-pentylcyclopentadienyl group, a η5-neopentylcyclopentadienyl group, a η5-n-hexylcyclopentadienyl group, a η5-n-octylcyclopentadienyl group, a η5-phenylcyclopentadienyl group, a η5-naphthylcyclopentadienyl group, a η5-trimethylsilylcyclopentadienyl group, a η5-triethylsilylcyclopentadienyl group, a η5-tert-butyldimethylsilylcyclopentadienyl group, a η5-indenyl group, a η5-methylindenyl group, a η5-dimethylindenyl group, a η5-ethylindenyl group, a η5-n-propylindenyl group, a η5-isopropylindenyl group, a η5-n-butylindenyl group, a η5-sec-butylindenyl group, a η5-tert-butylindenyl group, a η5-n-pentylindenyl group, a η5-neopentylindenyl group, a η5-n-hexylindenyl group, a η5-n-octylindenyl group, a η5-n-decylindenyl group, a η5-phenylindenyl group, a η5-methylphenylindenyl group, a η5-naphthylindenyl group, a η5-trimethylsilylindenyl group, a η5-triethylsilylindenyl group, a η5-tert-butyldimethylsilylindenyl group, a η5-tetrahydroindenyl group, a η5-fluorenyl group, a η5-methylfluorenyl group, a η5-dimethyl-fluorenyl group, a η5-ethylfluorenyl group, a η5-diethyl-fluorenyl group, a η5-n-propylfluorenyl group, a η5-di-n-propylfluorenyl group, a η5-isopropylfluorenyl group, a η5-diisopropylfluorenyl group, a η5-n-butylfluorenyl group, a η5-sec-butylfluorenyl group, a η5-tert-butylfluorenyl group, a η5-di-n-butylfluorenyl group, a η5-di-sec-butylfluorenyl group, a η5-di-tert-butylfluorenyl group, a η5-n-pentylfluorenyl group, a η5-neopentylfluorenyl group, a η5-n-hexylfluorenyl group, a η5-n-octylfluorenyl group, a η5-n-decylfluorenyl group, a η5-n-dodecylfluorenyl group, a η5-phenylfluorenyl group, a η5-di-phenylfluorenyl group, a η5-methylphenylfluorenyl group, a η5-naphthylfluorenyl group, a η5-trimethylsilylfluorenyl group, a η5-bistrimethylsilylfluorenyl group, a η5-triethylsilylfluorenyl group and a η5-tert-butyldimethylsilylfluorenyl group. Among them, a η5-cyclopentadienyl group, a η5-methylcyclopentadienyl group, a η5-tert-butylcyclopentadienyl group, a η5-tetramethylcyclopentadienyl group, a η5-indenyl group and a η5-fluorenyl group are preferable Examples of the transition metal complex (1) include the following compounds:
Transition metal complexes represented by the formula (1) wherein $B^1$ is a carbon atom: isopropylidene(cyclopentadienyl)(2-phenoxy)(1,3-butadiene)titanium, isopropylidene(cyclopentadienyl)(2-phenoxy)(1,3-pentadiene)titanium, isopropylidene-(cyclopentadienyl)(2-phenoxy)(2,4-hexadiene)titanium, isopropylidene(cyclopentadienyl)(2-phenoxy)(1,4-diphenyl-butadiene)titanium, isopropylidene-(cyclopentadienyl)(2-phenoxy)(2,3-dimethyl-1,3-butadiene)titanium, isopropylidene(cyclopentadienyl)(3,5-dimethyl-2-phenoxy)-(1,3-butadiene)titanium, isopropylidene-(cyclopentadienyl)(3,5-dimethyl-2-phenoxy)-(1,3-pentadiene)titanium, isopropylidene(cyclopentadienyl)(3,5-dimethyl-2-phenoxy)-(2,4-hexadiene)titanium, isopropylidene(cyclopentadienyl)(3,5-dimethyl-2-phenoxy)-(1,4-diphenylbutadiene)titanium, isopropylidene-(cyclopentadienyl)(3,5-dimethyl-2-phenoxy)-(2,3-dimethyl-1,3-butadiene)titanium, isopropylidene(cyclopentadienyl)(3-tert-butyl-5-methyl-2-phenoxy)(1,3-butadiene)titanium, isopropylidene-(cyclopentadienyl)(3-tert-butyl-5-methyl-2-phenoxy)(1,3-pentadiene)titanium, isopropylidene(cyclopentadienyl)(3-tert-butyl-5-methyl-2-phenoxy)(2,4-hexadiene)titanium, isopropylidene(cyclopentadienyl)(3-tert-butyl-5-methyl-2-phenoxy)(1,4-diphenylbutadiene)titanium, isopropylidene-(cyclopentadienyl)(3-tert-butyl-5-methyl-2-phenoxy)(2,3-dimethyl-1,3-butadiene)titanium, isopropylidene(cyclopentadienyl)(3,5-di-tert-butyl-2-phenoxy)(1,3-butadiene) titanium, isopropylidene-(cyclopentadienyl)(3,5-di-tert-butyl-2-phenoxy)(1,3-pentadiene) titanium, isopropylidene(cyclopentadienyl)(3,5-di-tert-butyl-2-phenoxy)(2,4-hexadiene)titanium, isopropylidene (cyclopentadienyl)(3,5-di-tert-butyl-2-phenoxy)(1,4-diphenylbutadiene)titanium, isopropylidene-(cyclopentadienyl)(3,5-di-tert-butyl-2-phenoxy)(2,3-dimethyl-1,3-butadiene)titanium, isopropylidene(cyclopentadienyl)(3-tert-butyl-5-methoxy-2-phenoxy)(1,3-butadiene)titanium, isopropylidene-(cyclopentadienyl)(3-tert-butyl-5-methoxy-2-phenoxy)(1,3-pentadiene)titanium, isopropylidene(cyclopentadienyl)(3-tert-butyl-5-methoxy-2-phenoxy)(2,4-hexadiene)titanium, isopropylidene(cyclopentadienyl)(3-tert-butyl-5-methoxy-2-phenoxy)(1,4-diphenylbutadiene)titanium, isopropylidene-(cyclopentadienyl)(3-tert-butyl-5-methoxy-2-phenoxy)(2,3-dimethyl-1,3-butadiene)titanium, isopropylidene(cyclopentadienyl)(3-phenyl-5-methyl-2-phenoxy)(1,3-butadiene)titanium, isopropylidene-(cyclopentadienyl)(3-phenyl-5-methyl-2-phenoxy)(1,3-pentadiene)titanium, isopropylidene(cyclopentadienyl)(3-phenyl-5-methyl-2-phenoxy)(2,4-hexadiene)titanium, isopropylidene (cyclopentadienyl)(3-phenyl-5-methyl-2-phenoxy)(1,4-diphenylbutadiene)titanium, isopropylidene-(cyclopentadienyl)(3-phenyl-5-methyl-2-phenoxy)(2,3-dimethyl-1,3-butadiene)titanium, isopropylidene(3-tert-butylcyclopentadienyl)(2-phenoxy)(1,3-butadiene)titanium, isopropylidene(3-tert-butylcyclopentadienyl)(2-phenoxy)(1,3-pentadiene)titanium, isopropylidene(3-tert-butylcyclopentadienyl)(2-phenoxy)-(2,4-hexadiene)titanium, isopropylidene(3-tert-butylcyclopentadienyl) (2-phenoxy)(1,4-diphenylbutadiene) titanium, isopropylidene(3-tert-butylcyclopentadienyl)(2-phenoxy)-2,3-dimethyl-1,3-butadiene)titanium, isopropylidene(3-tert-butylcyclopentadienyl)(3,5-dimethyl-2-phenoxy)(1,3-butadiene)titanium, isopropylidene-3-tert-butylcyclopentadienyl)(3,5-dimethyl-2-phenoxy)(1,3-pentadiene)titanium, isopropylidene(3-tert-butylcyclopentadienyl) (3,5-dimethyl-2-phenoxy) (2,4-hexadiene)-itanium, isopropylidene(3-tert-butylcyclopentadienyl)(3,5-dimethyl-2-phenoxy)(1,4-diphenylbutadiene)titanium, isopropylidene(3-tert-butylcyclopentadienyl)(3,5-dimethyl-2-phenoxy)(2,3-dimethyl-1,3-butadiene)titanium, isopropylidene(3-tert-butylcyclopentadienyl)(3-tert-butyl-5-methyl-2-phenoxy)(1,3-butadiene)titanium, isopropylidene(3-tert-butylcyclopentadienyl)(3-tert-butyl-5-methyl-2-phenoxy)(1,3-pentadiene)titanium, isopropylidene(3-tert-butylcyclopentadienyl)(3-tert-butyl-5-methyl-2-phenoxy)(2,4-hexadiene)titanium, isopropylidene-(3-tert-butylcyclopentadienyl)(3-tert-butyl-5-methyl-2-phenoxy)(1,4-diphenylbutadiene)titanium, isopropylidene(3-tert-butylcyclopentadienyl)(3-tert-butyl-5-methyl-2-phenoxy)(2,3-dimethyl-1,3-butadiene)titanium, isopropylidene(3-tert-butylcyclopentadienyl)(3,5-di-tert-butyl-2-phenoxy)(1,3-butadiene)titanium, isopropylidene(3-tert-butylcyclopentadienyl)(3,5-di-tert-butyl-2-phenoxy)(1,3-pentadiene)titanium, isopropylidene(3-tert-butylcyclopentadienyl)(3,5-di-tert-butyl-2-phenoxy)-(2,4-hexadiene)titanium, isopropylidene(3-tert-butylcyclopentadienyl)(3,5-di-tert-butyl-2-phenoxy)(1,4-diphenylbutadiene)titanium, isopropylidene(3-tert-butylcyclopentadienyl)(3,5-di-tert-butyl-2-phenoxy)(2,3-dimethyl-1,3-butadiene)titanium, isopropylidene(3-tert-butylcyclopentadienyl)(3-tert-butyl-5-methoxy-2-phenoxy)(1,3-butadiene)titanium, isopropylidene(3-tert-butylcyclopentadienyl)(3-tert-butyl-5-methoxy-2-phenoxy)(1,3-pentadiene)titanium, isopropylidene(3-tert-butylcyclopentadienyl)(3-tert-butyl-5-methoxy-2-phenoxy)(2,4-hexadiene)titanium, isopropylidene(3-tert-butylcyclopentadienyl)(3-tert-butyl-5-methoxy-2-phenoxy)(1,4-diphenylbutadiene)titanium, isopropylidene(3-tert-butylcyclopentadienyl)(3-tert-butyl-5-methoxy-2-phenoxy)(2,3-dimethyl-1,3-butadiene)titanium, isopropylidene(3-tert-butylcyclopentadienyl)(3-phenyl-5-methyl-2-phenoxy)(1,3-butadiene)titanium, isopropylidene(3-tert-butylcyclopentadienyl)(3-phenyl-5-methyl-2-phenoxy)(1,3-pentadiene)titanium, isopropylidene-(3-tert-butylcyclopentadienyl)(3-phenyl-5-methyl-2-phenoxy)(2,4-hexadiene)titanium, isopropylidene(3-tert-butylcyclopentadienyl)(3-phenyl-5-methyl-2-phenoxy)(1,4-diphenylbutadiene)titanium and isopropylidene(3-tert-butylcyclopentadienyl)(3-phenyl-5-methyl-2-phenoxy)(2,3-dimethyl-1,3-butadiene)titanium.

Transition metal complexes represented by the formula (1) wherein $B^1$ is an element, except for a carbon atom, belonging to the Group 14 of the periodic table of the elements: dimethylsilyl(cyclopentadienyl)(2-phenoxy)(1,3-butadiene)-titanium, dimethylsilyl(cyclopentadienyl)(2-phenoxy)(1,3-pentadiene)titanium, dimethylsilyl(cyclopentadienyl)(2-phenoxy)(2,4-hexadiene)titanium, dimethylsilyl-(cyclopentadienyl)(2-phenoxy)(1,4-diphenylbutadiene)-titanium, dimethylsilyl(cyclopentadienyl)(2-phenoxy)(2,3-dimethyl-1,3-butadiene)titanium, dimethylsilyl(cyclopentadienyl)(3,5-dimethyl-2-phenoxy)(1,3-butadiene)titanium, (cyclopentadienyl)(3,5-dimethyl-2-phenoxy)(1,3-pentadiene)titanium, dimethylsilyl(cyclopentadienyl)(3,5-dimethyl-2-phenoxy)(2,4-hexadiene)titanium, dimethylsilyl-(cyclopentadienyl)(3,5-dimethyl-2-phenoxy)(1,4-diphenyl-butadiene)titanium, dimethylsilyl(cyclopentadienyl)(3,5-dimethyl-2-phenoxy)(2,3-dimethyl-1,3-butadiene)titanium, dimethylsilyl(cyclopentadienyl)(3-tert-butyl-5-methyl-2-phenoxy)(1,3-butadiene)titanium, dimethylsilyl-(cyclopentadienyl)(3-tert-butyl-5-methyl-2-phenoxy)(1,3-pentadiene)titanium, dimethylsilyl(cyclopentadienyl)(3-tert-butyl-5-methyl-2-phenoxy)(2,4-hexadiene)titanium, dimethylsilyl(cyclopentadienyl)(3-tert-butyl-5-methyl-2-phenoxy)(1,4-diphenylbutadiene)titanium, dimethylsilyl-(cyclopentadienyl)(3-tert-butyl-5-methyl-2-phenoxy)(2,3-dimethyl-1,3-butadiene)titanium, dimethylsilyl(cyclopentadienyl)(3,5-di-tert-butyl-2-phenoxy)(1,3-butadiene)titanium, dimethylsilyl-(cyclopentadienyl)(3,5-di-tert-butyl-2-phenoxy)(1,3-pentadiene)titanium, dimethylsilyl(cyclopentadienyl)(3,5-di-tert-butyl-2-phenoxy)(2,4-hexadiene)titanium, dimethylsilyl(cyclopentadienyl)(3,5-di-tert-butyl-2-phenoxy)(1,4-diphenylbutadiene)titanium, dimethylsilyl-(cyclopentadienyl)(3,5-di-tert-butyl-2-phenoxy)(2,3-dimethyl-1,3-butadiene)titanium, dimethylsilyl(cyclopentadienyl)(3-tert-butyl-5-methoxy-2-phenoxy)(1,3-butadiene)titanium, dimethylsilyl-(cyclopentadienyl)(3-tert-butyl-5-methoxy-2-phenoxy)(1,3-pentadiene)titanium, dimethylsilyl(cyclopentadienyl)(3-tert-butyl-5-methoxy-2-phenoxy)(2,4-hexadiene)titanium, dimethylsilyl(cyclopentadienyl)(3-tert-butyl-5-methoxy-2-phenoxy)(1,4-diphenylbutadiene)titanium, dimethylsilyl-(cyclopentadienyl)(3-tert-butyl-5-methoxy-2-phenoxy)(2,3-dimethyl-1,3-butadiene)titanium, dimethylsilyl(cyclopentadienyl)(3-phenyl-5-methyl-2-phenoxy)(1,3-butadiene)titanium, dimethylsilyl-(cyclopentadienyl)(3-phenyl-5-methyl-2-phenoxy)(1,3-pentadiene)titanium, dimethylsilyl(cyclopentadienyl)(3-phenyl-5-methyl-2-phenoxy)(2,4-hexadiene)titanium, dimethylsilyl (cyclopentadienyl)(3-phenyl-5-methyl-2-phenoxy)(1,4-diphenylbutadiene)titanium, dimethylsilyl-(cyclopentadienyl)(3-phenyl-5-methyl-2-phenoxy)(2,3-dimethyl-1,3-butadiene)titanium, dimethylsilyl(2,3,4,5-tetramethyl-cyclopentadienyl)(2-phenoxy)(1,3-butadiene)titanium, dimethylsilyl(2,3,4,5-tetramethylcyclopentadienyl)-(2-phenoxy)(1,3-pentadiene)titanium, dimethylsilyl(2,3,4,5-tetramethylcyclopentadienyl)(2-phenoxy)(2,4-hexadiene)-titanium, dimethylsilyl(2,3,4,5-tetramethyl-cyclopentadienyl)(2-phenoxy)(1,4-diphenylbutadiene)titanium, dimethylsilyl(2,3,4,5-tetramethylcyclopentadienyl)-(2-phenoxy)(2,3-dimethyl-1,3-butadiene)titanium, dimethylsilyl(2,3,4,5-tetramethyl-cyclopentadienyl)(3,5-dimethyl-2-phenoxy)(1,3-butadiene)-titanium, dimethylsilyl (2,3,4,5-tetramethyl-cyclopentadienyl)(3,5-dimethyl-2-phenoxy)(1,3-pentadiene)-titanium, dimethylsilyl(2,3,4,5-tetramethyl-cyclopentadienyl)(3,5-dimethyl-2-phenoxy)(2,4-hexadiene)titanium, dimethylsilyl(2,3,4,5-tetramethyl-cyclopentadienyl)(3,5-dimethyl-2-phenoxy)(1,4-diphenyl-butadiene)titanium, dimethylsilyl(2,3,4,5-tetramethyl-cyclopentadienyl)(3,5-dimethyl-2-phenoxy)(2,3-dimethyl-1,3-butadiene)titanium, dimethylsilyl(2,3,4,5-tetramethyl-cyclopentadienyl)(3-tert-butyl-5-methyl-2-phenoxy)(1,3-butadiene)titanium, dimethylsilyl(2,3,4,5-tetramethyl-cyclopentadienyl)(3-tert-butyl-5-methyl-2-phenoxy)(1,3-pentadiene)titanium, dimethylsilyl(2,3,4,5-tetramethyl-cyclopenta-dienyl)(3-tert-butyl-5-methyl-2-phenoxy)(2,4-hexadiene)titanium, dimethylsilyl(2,3,4,5-tetramethyl-cyclopentadienyl)(3-tert-butyl-5-methyl-2-phenoxy)(1,4-diphenyl-butadiene)titanium, dimethylsilyl(2,3,4,5-tetramethyl-cyclopentadienyl)(3-tert-butyl-5-methyl-2-phenoxy)(2,3-dimethyl-1,3-butadiene)titanium, dimethylsilyl(2,3,4,5-tetramethyl-cyclopentadienyl)(3,5-di-tert-butyl-2-phenoxy)(1,3-butadiene)titanium, dimethylsilyl(2,3,4,5-tetramethylcyclopentadienyl)(3,5-di-tert-butyl-2-phenoxy)(1,3-pentadiene)titanium, dimethylsilyl(2,3,4,5-tetramethylcyclopentadienyl)(3,5-di-tert-butyl-2-phenoxy)(2,4-hexadiene)titanium, dimethylsilyl(2,3,4,5-tetramethylcyclopentadienyl)(3,5-di-tert-butyl-2-phenoxy)(1,4-diphenylbutadiene)titanium, dimethylsilyl-(2,3,4,5-tetramethylcyclopentadienyl)(3,5-di-tert-butyl-2-phenoxy)(2,3-dimethyl-1,3-butadiene)titanium, dimethylsilyl(2,3,4,5-tetramethyl-cyclopentadienyl)(3-tert-butyl-5-methoxy-2-phenoxy)(1,3-butadiene)titanium, dimethylsilyl(2,3,4,5-tetramethylcyclopentadienyl)(3-tert-butyl-5-methoxy-2-phenoxy)(1,3-pentadiene)titanium, dimethylsilyl(2,3,4,5-tetramethyl-cyclopentadienyl)(3-tert-butyl-5-methoxy-2-phenoxy)(2,4-hexadiene)titanium, dimethylsilyl(2,3,4,5-tetramethyl-cyclopentadienyl)(3-tert-butyl-5-methoxy-2-phenoxy)(1,4-diphenylbutadiene)titanium, dimethylsilyl(2,3,4,5-tetramethylcyclopentadienyl)(3-tert-butyl-5-methoxy-2-phenoxy)(2,3-dimethyl-1,3-butadiene)titanium, dimethylsilyl(2,3,4,5-tetramethyl-cyclopentadienyl)(3-phenyl-5-methyl-2-phenoxy)(1,3-butadiene)titanium, dimethylsilyl(2,3,4,5-tetramethyl-cyclopentadienyl)(3-phenyl-5-methyl-2-phenoxy)(1,3-pentadiene)titanium, dimethylsilyl(2,3,4,5-tetramethyl-cyclopentadienyl)(3-phenyl-5-methyl-2-phenoxy)(2,4-hexadiene)titanium, dimethylsilyl(2,3,4,5-tetramethyl-cyclopentadienyl)(3-phenyl-5-methyl-2-phenoxy)(1,4-diphenylbutadiene)titanium, dimethylsilyl(2,3,4,5-tetramethylcyclopentadienyl)(3-phenyl-5-methyl-2-phenoxy)(2,3-dimethyl-1,3-butadiene)titanium, dimethylsilyl(indenyl)(2-phenoxy)(1,3-butadiene)-titanium, dimethylsilyl(indenyl)(2-phenoxy)(1,3-pentadiene)titanium, dimethylsilyl(indenyl)(2-phenoxy)(2,4-hexadiene)titanium, dimethylsilyl(indenyl)(2-phenoxy)(1,4-diphenylbutadiene)titanium, dimethylsilyl(indenyl)(2-phenoxy)(2,3-dimethyl-1,3-butadiene)titanium, dimethylsilyl(indenyl)(3,5-dimethyl-2-phenoxy)(1,3-butadiene)titanium, dimethylsilyl(indenyl)-(3,5-dimethyl-2-phenoxy)(1,3-pentadiene)titanium, dimethylsilyl(indenyl)(3,5-dimethyl-2-phenoxy)(2,4-hexadiene)titanium, dimethylsilyl(indenyl)(3,5-dimethyl-2-phenoxy)(1,4-diphenylbutadiene)titanium, dimethylsilyl-(indenyl)(3,5-dimethyl-2-phenoxy)(2,3-dimethyl-1,3-butadiene)titanium, dimethylsilyl(indenyl)(3-tert-butyl-5-methyl-2-phenoxy)(1,3-butadiene)titanium, dimethylsilyl(indenyl)(3-tert-butyl-5-methyl-2-phenoxy)-(1,3-pentadiene)titanium, dimethylsilyl(indenyl)(3-tert-butyl-5-methyl-2-phenoxy)-(2,4-hexadiene)titanium, dimethylsilyl(indenyl)(3-tert-butyl-5-methyl-2-phenoxy)-(1,4-diphenylbutadiene)titanium, dimethylsilyl(indenyl)(3-tert-butyl-5-methyl-2-phenoxy)-(2,3-dimethyl-1,3-butadiene)titanium, dimethylsilyl(indenyl)(3,5-di-tert-butyl-2-phenoxy)(1,3-butadiene)titanium, dimethylsilyl(indenyl)-(3,5-di-tert-butyl-2-phenoxy)(1,3-pentadiene)titanium, dimethylsilyl(indenyl)(3,5-di-tert-butyl-2-phenoxy)(2,4-hexadiene)titanium, dimethylsilyl(indenyl)(3,5-di-tert-butyl-2-phenoxy)(1,4-diphenylbutadiene)titanium, dimethylsilyl(indenyl)(3,5-di-tert-butyl-2-phenoxy)(2,3-dimethyl-1,3-butadiene)titanium, dimethylsilyl(indenyl)(3-tert-butyl-5-methoxy-2-phenoxy)-(1,3-butadiene)titanium, dimethylsilyl(indenyl)(3-tert-butyl-5-methoxy-2-phenoxy)-(1,3-pentadiene)titanium, dimethylsilyl(indenyl)(3-tert-butyl-5-methoxy-2-phenoxy)-(2,4-hexadiene)titanium, dimethylsilyl(indenyl)(3-tert-butyl-5-methoxy-2-phenoxy)-(1,4-diphenylbutadiene)titanium, dimethylsilyl(indenyl)(3-tert-butyl-5-methoxy-2-phenoxy)-(2,3-dimethyl-1,3-butadiene)titanium, dimethylsilyl(indenyl)(3-phenyl-5-methyl-2-phenoxy)(1,3-butadiene)titanium, dimethylsilyl(indenyl)(3-phenyl-5-methyl-2-phenoxy)(1,3-pentadiene)titanium, dimethylsilyl(indenyl)(3-phenyl-5-methyl-2-phenoxy)(2,4-hexadiene)titanium, dimethylsilyl(indenyl)(3-phenyl-5-methyl-2-phenoxy)(1,4-diphenylbutadiene)titanium, dimethylsilyl(indenyl)(3-phenyl-5-methyl-2-phenoxy)(2,3-dimethyl-1,3-butadiene)titanium, dimethylsilyl(methylcyclopentadienyl)(2-phenoxy)(1,3-butadiene)titanium, dimethylsilyl-(methylcyclopentadienyl)(2-phenoxy)(1,3-pentadiene)titanium, dimethylsilyl(methylcyclopentadienyl)(2-phenoxy)(2,4-hexadiene)titanium, dimethylsilyl(methylcyclopentadienyl)-(2-phenoxy)(1,4-diphenylbutadiene)titanium, dimethylsilyl-(methylcyclopentadienyl)(2-phenoxy)(2,3-dimethyl-1,3-butadiene)titanium, dimethylsilyl(methylcyclopentadienyl)(3,5-dimethyl-2-phenoxy)(1,3-butadiene)titanium, dimethylsilyl-(methylcyclopentadienyl)(3,5-dimethyl-2-phenoxy)(1,3-pentadiene)titanium, dimethylsilyl(methylcyclopentadienyl)-(3,5-dimethyl-2-phenoxy)(2,4-hexadiene)titanium, dimethylsilyl(methylcyclopentadienyl)(3,5-dimethyl-2-phenoxy)(1,4-diphenylbutadiene)titanium, dimethylsilyl-(methylcyclopentadienyl)(3,5-dimethyl-2-phenoxy)(2,3-dimethyl-1,3-butadiene)titanium, dimethylsilyl(methylcyclopentadienyl)(3-tert-butyl-5-methyl-2-phenoxy)(1,3-butadiene)titanium, dimethylsilyl(methylcyclopentadienyl)(3-tert-butyl-5-methyl-2-phenoxy)(1,3-pentadiene)titanium, dimethylsilyl-(methylcyclopentadienyl)(3-tert-butyl-5-methyl-2-phenoxy)(2,4-hexadiene)titanium, dimethylsilyl-(methylcyclopentadienyl)(3-tert-butyl-5-methyl-2-phenoxy)(1,4-diphenylbutadiene)titanium, dimethylsilyl-(methylcyclopentadienyl)(3-tert-butyl-5-methyl-2-phenoxy)(2,3-dimethyl-1,3-butadiene)titanium, dimethylsilyl(methylcyclopentadienyl)(3,5-di-tert-butyl-2-phenoxy)(1,3-butadiene)titanium, dimethylsilyl(methylcyclopentadienyl)(3,5-di-tert-butyl-2-phenoxy)(1,3-pentadiene)titanium, dimethylsilyl-(methylcyclopentadienyl)(3,5-di-tert-butyl-2-phenoxy)(2,4-hexadiene)titanium, dimethylsilyl(methylcyclopentadienyl)-(3,5-di-tert-butyl-2-phenoxy)(1,4-diphenylbutadiene)-titanium, dimethylsilyl(methylcyclopentadienyl)(3,5-di-tert-butyl-2-phenoxy)(2,3-dimethyl-1,3-butadiene)titanium, dimethylsilyl(methylcyclopentadienyl)(3-tert-butyl-5-methoxy-2-phenoxy)(1,3-butadiene)titanium, dimethylsilyl(methylcyclopentadienyl)(3-tert-butyl-5-methoxy-2-phenoxy)(1,3-pentadiene)titanium, dimethylsilyl-(methylcyclopentadienyl)(3-tert-butyl-5-methoxy-2-phenoxy)-(2,4-hexadiene)titanium, dimethylsilyl(methylcyclopentadienyl)(3-tert-butyl-5-methoxy-2-phenoxy)(1,4-diphenyl-butadiene)titanium, dimethylsilyl(methylcyclopentadienyl)(3-tert-butyl-5-methoxy-2-phenoxy)(2,3-dimethyl-1,3-butadiene)titanium, dimethylsilyl(methylcyclopentadienyl)(3-phenyl-5-methyl-2-phenoxy)(1,3-butadiene)titanium, dimethylsilyl-(methylcyclopentadienyl)(3-phenyl-5-methyl-2-phenoxy)(1,3-pentadiene)titanium, dimethylsilyl(methylcyclopentadienyl)-(3-phenyl-5-methyl-2-phenoxy)(2,4-hexadiene)titanium, dimethylsilyl(methylcyclopentadienyl)(3-phenyl-5-methyl-2-phenoxy)(1,4-diphenylbutadiene)titanium, dimethylsilyl-(methylcyclopentadienyl)(3-phenyl-5-methyl-2-phenoxy)(2,3-dimethyl-1,3-butadiene)titanium, dimethylsilyl(3-tert-butylcyclopentadienyl)(2-phenoxy)(1,3-butadiene)titanium, dimethylsilyl(3-tert-butylcyclopentadienyl)(2-phenoxy)(1,3-pentadiene)titanium, dimethylsilyl(3-tert-butylcyclopentadienyl)(2-phenoxy)(2,4-hexadiene)titanium, dimethylsilyl(3-tert-butylcyclopentadienyl) (2-phenoxy)(1,4-diphenylbutadiene)titanium, dimethylsilyl(3-tert-butylcyclopentadienyl)(2-phenoxy)(2,3-dimethyl-1,3-butadiene)titanium, dimethylsilyl(3-tert-butylcyclopentadienyl)(3,5-dimethyl-2-phenoxy)(1,3-butadiene)titanium, dimethylsilyl-(3-tert-butylcyclopentadienyl)(3,5-dimethyl-2-phenoxy)(1,3-pentadiene)titanium, dimethylsilyl(3-tert-butylcyclopentadienyl) (3,5-dimethyl-2-phenoxy)(2,4-hexadiene)titanium, dimethylsilyl(3-tert-butylcyclopentadienyl)(3,5-dimethyl-2-phenoxy)(1,4-diphenylbutadiene)titanium, dimethylsilyl(3-tert-butylcyclopentadienyl)(3,5-dimethyl-2-phenoxy)(2,3-dimethyl-1,3-butadiene)titanium, dimethylsilyl(3-tert-butylcyclopentadienyl)(3-tert-butyl-5-methyl-2-phenoxy)(1,3-butadiene)titanium, dimethylsilyl(3-tert-butylcyclopentadienyl)(3-tert-butyl-5-methyl-2-phenoxy)(1,3-pentadiene)titanium, dimethylsilyl(3-tert-butylcyclopentadienyl)(3-tert-butyl-5-methyl-2-phenoxy)(2,4-hexadiene)titanium, dimethylsilyl(3-tert-butylcyclopentadienyl)(3-tert-butyl-5-methyl-2-phenoxy)-(1,4-diphenylbutadiene)titanium, dimethylsilyl(3-tert-butylcyclopentadienyl)(3-tert-butyl-5-methyl-2-phenoxy)-(2,3-dimethyl-1,3-butadiene)titanium, dimethylsilyl(3-tert-butylcyclopentadienyl)(3,5-di-tert-butyl-2-phenoxy)(1,3-butadiene)titanium, dimethylsilyl(3-tert-butylcyclopentadienyl)(3,5-di-tert-butyl-2-phenoxy)(1,3-pentadiene)titanium, dimethylsilyl(3-tert-butylcyclopentadienyl)(3,5-di-tert-butyl-2-phenoxy)-(2,4-hexadiene)titanium, dimethylsilyl(3-tertbutylcyclopentadienyl)(3,5-di-tert-butyl-2-phenoxy)(1,4-diphenylbutadiene)titanium, dimethylsilyl(3-tert-butylcyclopentadienyl)(3,5-di-tert-butyl-2-phenoxy)(2,3-dimethyl-1,3-butadiene)titanium,
dimethylsilyl(3-tert-butylcyclopentadienyl)(3-tert-butyl-5-methoxy-2-phenoxy)(1,3-butadiene)titanium, dimethylsilyl(3-tert-butylcyclopentadienyl)(3-tert-butyl-5-methoxy-2-phenoxy)(1,3-pentadiene)titanium, dimethylsilyl-(3-tert-butylcyclopentadienyl)(3-tert-butyl-5-methoxy-2-phenoxy)(2,4-hexadiene)titanium, dimethylsilyl(3-tert-butylcyclopentadienyl)(3-tert-butyl-5-methoxy-2-phenoxy)-(1,4-diphenylbutadiene)titanium, dimethylsilyl(3-tert-butylcyclopentadienyl)(3-tert-butyl-5-methoxy-2-phenoxy)(2,3-dimethyl-1,3-butadiene)titanium,
dimethylsilyl(3-tert-butylcyclopentadienyl)(3-phenyl-5-methyl-2-phenoxy)(1,3-butadiene)titanium, dimethylsilyl(3-tert-butylcyclopentadienyl)(3-phenyl-5-methyl-2-phenoxy)(1,3-pentadiene)titanium, dimethylsilyl(3-tert-butylcyclopentadienyl)(3-phenyl-5-methyl-2-phenoxy)-(2,4-hexadiene)titanium, dimethylsilyl(3-tert-butyl-cyclopentadienyl)(3-phenyl-5-methyl-2-phenoxy)(1,4-diphenylbutadiene)titanium and dimethylsilyl(3-tert-butylcyclopentadienyl)(3-phenyl-5-methyl-2-phenoxy)(2,3-dimethyl-1,3-butadiene)titanium, and
the above compounds in which dimethylsilyl is replaced by diethylsilyl, diphenylsilyl or dimethoxysilyl, the above compounds in which titanium is replaced by zirconium or hafnium and the above compounds in which chloride is replaced by bromide or iodide.

The transition metal complex (1) can be produced by reacting a halogenated transition metal complex of the following formula (2) with a 1,3-diene compound of the following formula (3) in the presence of an alkali metal or an alkali metal compound, or an alkaline earth metal or an alkaline earth metal compound:

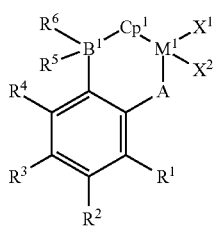

(2)

wherein A, $B^1$, $M^1$, $Cp^1$, $R^1$, $R^2$, $R^3$, $R^4$, $R^5$ and $R^6$ are the same as defined above; and $X^1$ and $X^2$ represent independently of one another a halogen atom, and

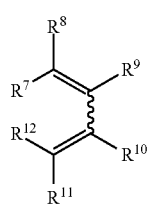

(3)

wherein $R^7$, $R^8$, $R^9$, $R^{10}$, $R^{11}$ and $R^{12}$ are the same as defined above; and the 1,3-diene structure may be of either a cis or trans form, or a mixed form thereof.

Examples of the halogenated transition metal complex of the formula (2) include the following compounds: Transition metal complexes represented by the formula (2) wherein $B^1$ is a carbon atom: methylene(cyclopentadienyl)(3,5-dimethyl-2-phenoxy)titanium dichloride, methylene(cyclopentadienyl)(3-tert-butyl-2-phenoxy)titanium dichloride, methylene (cyclopentadienyl)(3-tert-butyl-5-methyl-2-phenoxy) titanium dichloride, methylene(cyclopentadienyl)(3-phenyl-2-phenoxy)titanium dichloride, methylene (cyclopentadienyl)(3-tert-butyl-dimethylsilyl-5-methyl-2-phenoxy)titanium dichloride, methylene(cyclopentadienyl) (3-trimethylsilyl-5-methyl-2-phenoxy)titanium dichloride, methylene(cyclopentadienyl)(3-tert-butyl-5-methoxy-2-phenoxy)titanium dichloride, methylene(cyclopentadienyl) (3-tert-butyl-5-chloro-2-phenoxy)titanium dichloride,
methylene(methylcyclopentadienyl)(3,5-dimethyl-2-phenoxy)titanium dichloride, methylene(methylcyclopentadienyl) (3-tert-butyl-2-phenoxy)titanium dichloride, methylene(methylcyclopentadienyl)(3-tert-butyl-5-methyl-2-phenoxy)titanium dichloride, methylene (methylcyclopentadienyl) (3-phenyl-2-phenoxy)titanium dichloride, methylene-(methylcyclopentadienyl)(3-tert-butyldimethylsilyl-5-methyl-2-phenoxy)titanium dichloride, methylene-(methylcyclopentadienyl)(3-trimethylsilyl-5-methyl-2-phenoxy)titanium dichloride, methylene(methylcyclopentadienyl) (3-tert-butyl-5-methoxy-2-phenoxy)titanium dichloride, methylene(methylcyclopentadienyl)(3-tert-butyl-5-chloro-2-phenoxy)titanium dichloride,
methylene(tert-butylcyclopentadienyl)(3,5-dimethyl-2-phenoxy)titanium dichloride, methylene(tert-butylcyclopentadienyl)(3-tert-butyl-2-phenoxy)titanium dichloride, methylene(tert-butylcyclopentadienyl)(3-tert-butyl-5-methyl-2-phenoxy)titanium dichloride, methylene-(tert-butylcyclopentadienyl)(3-phenyl-2-phenoxy)titanium dichloride, methylene(tert-butylcyclopentadienyl)(3-tert-butyldimethyl-silyl-5-methyl-2-phenoxy)titanium dichloride, methylene(tert-butylcyclopentadienyl)(3-trimethylsilyl-5-methyl-2-phenoxy)titanium dichloride, methylene(tert-butylcyclopentadienyl)(3-tert-butyl-5-methoxy-2-phenoxy)-titanium dichloride, methylene(tert-butylcyclopentadienyl) (3-tert-butyl-5-chloro-2-phenoxy)titanium dichloride,
methylene(tetramethylcyclopentadienyl)(3,5-dimethyl-2-phenoxy)titanium dichloride, methylene-(tetramethylcyclopentadienyl)(3-tert-butyl-2-phenoxy)-titanium dichloride, methylene(tetramethylcyclopentadienyl) (3-tert-butyl-5-methyl-2-phenoxy)titanium dichloride, methylene(tetramethylcyclopentadienyl)(3-phenyl-2-phenoxy)-titanium dichloride, methylene(tetramethylcyclopentadienyl) (3-tert-butyldimethyl-silyl-5-methyl-2-phenoxy)-titanium dichloride, methylene(tetramethylcyclopentadienyl) (3-trimethylsilyl-5-methyl-2-phenoxy)titanium dichloride, methylene(tetramethylcyclopentadienyl)(3-tert-butyl-5-methoxy-2-phenoxy)titanium dichloride, methylene-(tetramethylcyclopentadienyl)(3-tert-butyl-5-chloro-2-phenoxy)titanium dichloride,
methylene(trimethylsilylcyclopentadienyl)(3,5-dimethyl-2-phenoxy)titanium dichloride, methylene-(trimethylsilyl-cyclopentadienyl)(3-tert-butyl-2-phenoxy)-titanium dichloride, methylene(trimethylsilylcyclopentadienyl) (3-tert-butyl-5-methyl-2-phenoxy)titanium dichloride, methylene (trimethylsilylcyclopentadienyl)(3-phenyl-2-phenoxy) titanium dichloride, methylene(trimethylsilyl-cyclopentadienyl)(3-tert-butyl-dimethylsilyl-5-methyl-2-phenoxy)titanium dichloride, methylene (trimethylsilylcyclopentadienyl) (3-trimethylsilyl-5-methyl-2-phenoxy)-titanium dichloride, methylene (trimethylsilylcyclopentadienyl) (3-tert-butyl-5-methoxy-2- phenoxy)titanium dichloride, methylene(trimethylsilylcyclopentadienyl)(3-tert-butyl-5-chloro-2-phenoxy)titanium dichloride, methylene(fluorenyl)(3,5-dimethyl-2-phenoxy)-titanium dichloride, methylene(fluorenyl)(3-tert-butyl-2-phenoxy)titanium dichloride, methylene(fluorenyl)(3-tert-butyl-5-methyl-2-phenoxy)titanium dichloride, methylene-(fluorenyl)(3-phenyl-2-phenoxy)titanium dichloride, methylene(fluorenyl)(3-tert-butyldimethylsilyl-5-methyl-2-phenoxy)titanium dichloride, methylene(fluorenyl)(3-trimethylsilyl-5-methyl-2-phenoxy)titanium dichloride, methylene(fluorenyl)(3-tert-butyl-5-methoxy-2-phenoxy)-titanium dichloride, methylene(fluorenyl)(3-tert-butyl-5-chloro-2-phenoxy)titanium dichloride, isopropylidene(cyclopentadienyl)(3,5-dimethyl-2-phenoxy)titanium dichloride, isopropylidene-(cyclopentadienyl)(3-tert-butyl-2-phenoxy)titanium dichloride, isopropylidene(cyclopentadienyl)(3-tert-butyl-5-methyl-2-phenoxy)titanium dichloride, isopropylidene-(cyclopentadienyl)(3-phenyl-2-phenoxy)titanium dichloride, isopropylidene(cyclopentadienyl)(3-tert-butyldimethylsilyl-5-methyl-2-phenoxy)titanium dichloride, isopropylidene-(cyclopentadienyl)(3-trimethylsilyl-5-methyl-2-phenoxy)-titanium dichloride, isopropylidene(cyclopentadienyl)(3-tert-butyl-5-methoxy-2-phenoxy)titanium dichloride, isopropylidene(cyclopentadienyl)(3-tert-butyl-5-chloro-2-phenoxy)titanium dichloride, isopropylidene(methylcyclopentadienyl)(3,5-dimethyl-2-phenoxy)titanium dichloride, isopropylidene-(methylcyclopentadienyl)(3-tert-butyl-2-phenoxy)titanium dichloride, isopropylidene(methylcyclopentadienyl)(3-tert-butyl-5-methyl-2-phenoxy)titanium dichloride, isopropylidene(methylcyclopentadienyl)(3-phenyl-2-phenoxy)titanium dichloride, isopropylidene-(methylcyclopentadienyl)(3-tert-butyldimethyl-silyl-5-methyl-2-phenoxy)titanium dichloride, isopropylidene-(methylcyclopentadienyl)(3-trimethylsilyl-5-methyl-2-phenoxy)titanium dichloride, isopropylidene-(methylcyclopentadienyl)(3-tert-butyl-5-methoxy-2-phenoxy)-titanium dichloride, isopropylidene(methylcyclopentadienyl) (3-tert-butyl-5-chloro-2-phenoxy) titanium dichloride, isopropylidene(tert-butylcyclopentadienyl)(3,5-dimethyl-2-phenoxy)titanium dichloride, isopropylidene-(tert-butylcyclopentadienyl)(3-tert-butyl-2-phenoxy)-titanium dichloride, isopropylidene(tert-butylcyclopentadienyl) (3-tert-butyl-5-methyl-2-phenoxy)titanium dichloride, isopropylidene(tert-butylcyclopentadienyl)(3-phenyl-2-phenoxy)titanium dichloride, isopropylidene(tert-butyl-cyclopentadienyl)(3-tert-butyl-dimethylsilyl-5-methyl-2-phenoxy)titanium dichloride, isopropylidene(tert-butyl-cyclopentadienyl)(3-trimethylsilyl-5-methyl-2-phenoxy)-titanium dichloride, isopropylidene(tert-butylcyclopentadienyl) (3-tert-butyl-5-methoxy-2-phenoxy) titanium dichloride, isopropylidene(tert-butylcyclopentadienyl)(3-tert-butyl-5-chloro-2-phenoxy) titanium dichloride, isopropylidene(tetramethylcyclopentadienyl)(3,5-dimethyl-2-phenoxy)titanium dichloride, isopropylidene-(tetramethylcyclopentadienyl)(3-tert-butyl-2-phenoxy)-titanium dichloride, isopropylidene(tetramethylcyclopentadienyl)(3-tert-butyl-5-methyl-2-phenoxy) titanium dichloride, isopropylidene (tetramethylcyclopentadienyl)(3-phenyl-2-phenoxy) titanium dichloride, isopropylidene-(tetramethylcyclopentadienyl)(3-tert-butyl-dimethylsilyl-5-methyl-2-phenoxy)titanium dichloride, isopropylidene-(tetramethylcyclopentadienyl)(3-trimethylsilyl-5-methyl-2-phenoxy)titanium dichloride, isopropylidene(tetramethylcyclopentadienyl)(3-tert-butyl-5-methoxy-2-phenoxy) titanium dichloride, isopropylidene (tetramethylcyclopentadienyl)(3-tert-butyl-5-chloro-2-phenoxy)titanium dichloride, isopropylidene(trimethylsilylcyclopentadienyl)-(3,5-dimethyl-2-phenoxy)titanium dichloride, isopropylidene(trimethylsilylcyclopentadienyl)(3-tert-butyl-2-phenoxy)titanium dichloride, isopropylidene-(trimethylsilylcyclopentadienyl)(3-tert-butyl-5-methyl-2-phenoxy)titanium dichloride, isopropylidene-(trimethylsilylcyclopentadienyl)(3-phenyl-2-phenoxy)-titanium dichloride, isopropylidene(trimethylsilyl-cyclopentadienyl)(3-tert-butyl-dimethylsilyl-5-methyl-2-phenoxy)titanium dichloride, isopropylidene(trimethylsilyl-cyclopentadienyl)(3-trimethyl-silyl-5-methyl-2-phenoxy)-titanium dichloride, isopropylidene(trimethylsilyl-cyclopentadienyl)(3-tert-butyl-5-methoxy-2-phenoxy)titanium dichloride, isopropylidene(trimethylsilylcyclopentadienyl)-(3-tert-butyl-5-chloro-2-phenoxy)titanium dichloride, isopropylidene(fluorenyl)(3,5-dimethyl-2-phenoxy)titanium dichloride, isopropylidene(fluorenyl)(3-tert-butyl-2-phenoxy)titanium dichloride, isopropylidene-(fluorenyl)(3-tert-butyl-5-methyl-2-phenoxy)titanium dichloride, isopropylidene(fluorenyl)(3-phenyl-2-phenoxy)-titanium dichloride, isopropylidene(fluorenyl)(3-tert-butyldimethylsilyl-5-methyl-2-phenoxy)titanium dichloride, isopropylidene(fluorenyl)(3-trimethylsilyl-5-methyl-2-phenoxy)titanium dichloride, isopropylidene(fluorenyl)(3-tert-butyl-5-methoxy-2-phenoxy)titanium dichloride, isopropylidene(fluorenyl)(3-tert-butyl-5-chloro-2-phenoxy)-titanium dichloride, diphenylmethylene(cyclopentadienyl)(3,5-dimethyl-2-phenoxy)titanium dichloride, diphenylmethylene-(cyclopentadienyl)(3-tert-butyl-2-phenoxy)titanium dichloride, diphenylmethylene(cyclopentadienyl)(3-tert-butyl-5-methyl-2-phenoxy)titanium dichloride, diphenylmethylene(cyclopentadienyl)(3-phenyl-2-phenoxy)-titanium dichloride, diphenylmethylene(cyclopentadienyl)(3-tert-butyldimethyl-silyl-5-methyl-2-phenoxy)titanium dichloride, diphenylmethylene(cyclopentadienyl)(3-trimethylsilyl-5-methyl-2-phenoxy)titanium dichloride, diphenylmethylene(cyclopentadienyl)(3-tert-butyl-5-methoxy-2-phenoxy)titanium dichloride, diphenylmethylene-(cyclopentadienyl)(3-tert-butyl-5-chloro-2-phenoxy)titanium dichloride, diphenylmethylene(methylcyclopentadienyl)(3,5-dimethyl-2-phenoxy)titanium dichloride, diphenylmethylene-(methylcyclopentadienyl)(3-tert-butyl-2-phenoxy)titanium dichloride, diphenylmethylene(methylcyclopentadienyl)(3-tert-butyl-5-methyl-2-phenoxy)titanium dichloride, diphenylmethylene(methylcyclopentadienyl)(3-phenyl-2-phenoxy)titanium dichloride, diphenylmethylene-(methylcyclopentadienyl)(3-tert-butyl-dimethylsilyl-5-methyl-2-phenoxy)titanium dichloride, diphenylmethylene-(methylcyclopentadienyl)(3-trimethylsilyl-5-methyl-2-phenoxy)titanium dichloride, diphenylmethylene-(methylcyclopentadienyl)(3-tert-butyl-5-methoxy-2-phenoxy)titanium dichloride, diphenylmethylene-(methylcyclopentadienyl)(3-tert-butyl-5-chloro-2-phenoxy) titanium dichloride, diphenylmethylene(tert-butylcyclopentadienyl)-(3,5-dimethyl-2-phenoxy)titanium dichloride, diphenylmethylene (tert-butylcyclopentadienyl)(3-tert-butyl-2-phenoxy)titanium dichloride, diphenylmethylene(tert-butylcyclopentadienyl)(3-tert-butyl-5-methyl-2-phenoxy)-titanium dichloride, diphenylmethylene(tert-butylcyclopentadienyl)(3-phenyl-2-phenoxy)titanium dichloride, diphenylmethylene(tert-butylcyclopentadienyl)(3-tert-butyl-dimethylsilyl-5-methyl-2-phenoxy)titanium dichloride, diphenylmethylene(tert-butylcyclopentadienyl)(3-trimethylsilyl-5-methyl-2-phenoxy)titanium dichloride, diphenylmethylene(tert-butylcyclopentadienyl)(3-tert-butyl-5-methoxy-2-phenoxy)titanium dichloride, diphenylmethylene-(tert-butylcyclopentadienyl)(3-tert-butyl-5-chloro-2-phenoxy)titanium dichloride, diphenylmethylene(tetramethylcyclopentadienyl)-(3,5-dimethyl-2-phenoxy)titanium dichloride, diphenylmethylene(tetramethylcyclopentadienyl)(3-tert-butyl-2-phenoxy)titanium dichloride, diphenylmethylene-(tetramethylcyclopentadienyl)(3-tert-butyl-5-methyl-2-phenoxy)titanium dichloride, diphenylmethylene-(tetramethylcyclopentadienyl)(3-phenyl-2-phenoxy)titanium dichloride, diphenylmethylene(tetramethylcyclopentadienyl) (3-tert-butyl-dimethylsilyl-5-methyl-2-phenoxy)-titanium dichloride, diphenylmethylene(tetramethyl-cyclopentadienyl)(3-trimethyl-silyl-5-methyl-2-phenoxy)-titanium dichloride, diphenylmethylene(tetramethyl-cyclopentadienyl)(3-tert-butyl-5-methoxy-2-phenoxy)titanium dichloride, diphenylmethylene(tetramethylcyclopentadienyl)-(3-tert-butyl-5-chloro-2-phenoxy)titanium dichloride, diphenylmethylene(trimethylsilylcyclopentadienyl) (3,5-dimethyl-2-phenoxy)titanium dichloride, diphenylmethylene(trimethylsilylcyclopentadienyl)(3-tert-butyl-2-phenoxy)titanium dichloride, diphenylmethylene-(trimethylsilylcyclopentadienyl)(3-tert-butyl-5-methyl-2-phenoxy)titanium dichloride, diphenylmethylene-(trimethylsilylcyclopentadienyl)(3-phenyl-2-phenoxy)-titanium dichloride, diphenylmethylene(trimethylsilyl-cyclopentadienyl)(3-tert-butyldimethylsilyl-5-methyl-2-phenoxy)titanium dichloride, diphenylmethylene-(trimethylsilylcyclopentadienyl)-(3-trimethylsilyl-5-methyl-2-phenoxy)titanium dichloride, diphenylmethylene-(trimethylsilylcyclopentadienyl)(3-tert-butyl-5-methoxy-2-phenoxy)titanium dichloride, diphenylmethylene-(trimethylsilylcyclopentadienyl)(3-tert-butyl-5-chloro-2-phenoxy)titanium dichloride, diphenylmethylene(fluorenyl)(3,5-dimethyl-2-phenoxy) titanium dichloride, diphenylmethylene(fluorenyl)-(3-tert-butyl-2-phenoxy)titanium dichloride, diphenylmethylene (fluorenyl)(3-tert-butyl-5-methyl-2-phenoxy)titanium dichloride, diphenylmethylene(fluorenyl)-(3-phenyl-2-phenoxy)titanium dichloride, diphenylmethylene-(fluorenyl)(3-tert-butyldimethylsilyl-5-methyl-2-phenoxy)-titanium dichloride, diphenylmethylene(fluorenyl)(3-trimethylsilyl-5-methyl-2-phenoxy)titanium dichloride, diphenylmethylene(fluorenyl)(3-tert-butyl-5-methoxy-2-phenoxy)titanium dichloride, diphenylmethylene(fluorenyl)-(3-tert-butyl-5-chloro-2-phenoxy)titanium dichloride, the above compounds in which titanium is replaced by zirconium or hafnium, the above compounds in which chloride is replaced by bromide or iodide, the above compounds in which (cyclopentadienyl) is replaced by (dimethyl-cyclopentadienyl), (trimethylcyclopentadienyl), (n-butylcyclopentadienyl), (tert-butyldimethylsilyl-cyclopentadienyl) or (indenyl), the above compounds in which 3,5-dimethyl-2-phenoxy is replaced by 2-phenoxy, 3-methyl-2-phenoxy, 3,5-di-tert-butyl-2-phenoxy, 3-phenyl-5-methyl-2-phenoxy, 3-tert-butyldimethylsilyl-2-phenoxy or 3-trimethylsilyl-2-phenoxy, and the above compounds in which methylene is replaced by diethylmethylene.

Transition metal complexes represented by the formula (2) wherein $B^1$ is an element, except for a carbon atom, belonging to the Group 14 of the periodic table of the elements:

dimethylsilyl(cyclopentadienyl)(2-phenoxy)titanium dichloride, dimethylsilyl(cyclopentadienyl)(3-methyl-2-phenoxy)titanium dichloride, dimethylsilyl-(cyclopenta-dienyl)(3,5-dimethyl-2-phenoxy)titanium dichloride, dimethylsilyl(cyclopentadienyl)(3-tert-butyl-2-phenoxy)-titanium dichloride, dimethylsilyl-(cyclopentadienyl)(3-tert-butyl-5-methyl-2-phenoxy)titanium dichloride, dimethylsilyl(cyclopentadienyl)(3,5-di-tert-butyl-2-phenoxy)titanium dichloride, dimethylsilyl(cyclopenta-dienyl)(5-methyl-3-phenyl-2-phenoxy)titanium dichloride, dimethylsilyl (cyclopentadienyl)(3-tert-butyldimethylsilyl-5-methyl-2-phenoxy)titanium dichloride, dimethylsilyl-(cyclopentadienyl)(5-methyl-3-trimethylsilyl-2-phenoxy) titanium dichloride, dimethylsilyl-(cyclopentadienyl)-(3-tert-butyl-5-methoxy-2-phenoxy)-titanium dichloride, dimethylsilyl(cyclopentadienyl)(3-tert-butyl-5-chloro-2-phenoxy)titanium dichloride, dimethylsilyl-(cyclopentadienyl)(3,5-diamyl-2-phenoxy)titanium dichloride, dimethylsilyl(methylcyclopentadienyl)(2-phenoxy)-titanium dichloride, dimethylsilyl(methylcyclopentadienyl)-(3-methyl-2-phenoxy)titanium dichloride, dimethylsilyl-(methylcyclopentadienyl)(3,5-dimethyl-2-phenoxy)titanium dichloride, dimethylsilyl-(methylcyclopentadienyl)(3-tert-butyl-2-phenoxy)titanium dichloride, dimethylsilyl-(methylcyclopentadienyl)(3-tert-butyl-5-methyl-2-phenoxy)-titanium dichloride, dimethylsilyl(methylcyclopentadienyl)-(3, 5-di-tert-butyl-2-phenoxy)titanium dichloride, dimethylsilyl (methylcyclopentadienyl)-(5-methyl-3-phenyl-2-phenoxy) titanium dichloride, dimethylsilyl(methylcyclopentadienyl) (3-tert-butyldimethyl-silyl-5-methyl-2-phenoxy)titanium dichloride, dimethylsilyl(methylcyclopentadienyl) (5-methyl-3-trimethylsilyl-2-phenoxy)titanium dichloride, dimethylsilyl-(methylcyclopentadienyl)(3-tert-butyl-5-methoxy-2-phenoxy)titanium dichloride, dimethylsilyl (methylcyclopentadienyl)(3-tert-butyl-5-chloro-2-phenoxy) titanium dichloride, dimethylsilyl-(methylcyclopentadienyl) (3,5-diamyl-2-phenoxy)titanium dichloride, dimethylsilyl(n-butylcyclopentadienyl)(2-phenoxy)titanium dichloride, dimethylsilyl(n-butyl-cyclopentadienyl)(3-methyl-2-phenoxy)titanium dichloride, dimethylsilyl(n-butylcyclopentadienyl)(3,5-dimethyl-2-phenoxy)titanium dichloride, dimethylsilyl(n-butyl-cyclopentadienyl)(3-tert-butyl-2-phenoxy)titanium dichloride, dimethylsilyl(n-butyl-cyclopentadienyl)(3-tert-butyl-5-methyl-2-phenoxy)titanium dichloride, dimethylsilyl(n-butylcyclopentadienyl)(3, 5-di-tert-butyl-2-phenoxy)titanium dichloride, dimethylsilyl (n-butyl-cyclopentadienyl)(5-methyl-3-phenyl-2-phenoxy) titanium dichloride, dimethylsilyl(n-butylcyclopentadienyl) (3-tert-butyldimethyl-silyl-5-methyl-2-phenoxy)titanium dichloride, dimethylsilyl(n-butylcyclopentadienyl)(5-methyl-3-trimethylsilyl-2-phenoxy)titanium dichloride, dimethylsilyl(n-butylcyclopentadienyl)(3-tert-butyl-5-methoxy-2-phenoxy)titanium dichloride, dimethylsilyl(n-butylcyclopentadienyl)(3-tert-butyl-5-chloro-2-phenoxy)-titanium dichloride, dimethylsilyl(n-butylcyclopentadienyl) (3,5-diamyl-2-phenoxy)titanium dichloride, dimethylsilyl(tert-butylcyclopentadienyl)(2-phenoxy)titanium dichloride, dimethylsilyl(tert-butyl-cyclopentadienyl) (3-methyl-2-phenoxy)titanium dichloride, dimethylsilyl (tert-butylcyclopentadienyl)(3,5-dimethyl-2-phenoxy) titanium dichloride, dimethylsilyl(tert-butyl-cyclopentadienyl)(3-tert-butyl-2-phenoxy)titanium dichloride, dimethylsilyl(tert-butylcyclopentadienyl)(3-tert-butyl-5-methyl-2-phenoxy)titanium dichloride, dimethylsilyl(tert-butylcyclopentadienyl)(3,5-di-tert-butyl-2-phenoxy) titanium dichloride, dimethylsilyl(tert-butylcyclopentadienyl)(5-methyl-3-phenyl-2-phenoxy)

titanium dichloride, dimethylsilyl(tert-butylcyclopentadienyl)(3-tert-butyl-dimethylsilyl-5-methyl-2-phenoxy)titanium dichloride, dimethylsilyl(tert-butylcyclopentadienyl)(5-methyl-3-trimethylsilyl-2-phenoxy)titanium dichloride, dimethylsilyl(tert-butylcyclopentadienyl)(3-tert-butyl-5-methoxy-2-phenoxy) titanium dichloride, dimethylsilyl(tert-butylcyclopentadienyl)(3-tert-butyl-5-chloro-2-phenoxy)-titanium dichloride, dimethylsilyl(tert-butyl-cyclopentadienyl)(3,5-diamyl-2-phenoxy)titanium dichloride, dimethylsilyl(tetramethylcyclopentadienyl)(2-phenoxy) titanium dichloride, dimethylsilyl(tetramethyl-cyclopentadienyl)(3-methyl-2-phenoxy)titanium dichloride, dimethylsilyl(tetramethylcyclopentadienyl)(3,5-dimethyl-2-phenoxy) titanium dichloride, dimethylsilyl(tetramethyl-cyclopentadienyl)(3-tert-butyl-2-phenoxy)titanium dichloride, dimethylsilyl(tetramethylcyclopentadienyl)(3-tent-butyl-5-methyl-2-phenoxy)titanium dichloride, dimethylsilyl(tetramethylcyclopentadienyl)(3,5-di-tert-butyl-2-phenoxy)titanium dichloride, dimethylsilyl-(tetramethylcyclopentadienyl)(5-methyl-3-phenyl-2-phenoxy)-titanium dichloride, dimethylsilyl(tetramethyl-cyclopentadienyl)(3-tert-butyl-dimethylsilyl-5-methyl-2-phenoxy)titanium dichloride, dimethylsilyl(tetramethyl-cyclopentadienyl)(5-methyl-3-trimethylsilyl-2-phenoxy)-titanium dichloride, dimethylsilyl(tetramethyl-cyclopentadienyl)(3-tert-butyl-5-methoxy-2-phenoxy) titanium dichloride, dimethylsilyl (tetramethylcyclopentadienyl)(3-tert-butyl-5-chloro-2-phenoxy)titanium dichloride, dimethylsilyl (tetramethylcyclopentadienyl)(3,5-diamyl-2-phenoxy) titanium dichloride, dimethylsilyl(trimethylsilylcyclopentadienyl)(2-phenoxy)titanium dichloride, dimethylsilyl(trimethylsilyl-cyclopentadienyl)(3-methyl-2-phenoxy)titanium dichloride, dimethylsilyl(trimethylsilylcyclopentadienyl)(3,5-dimethyl-2-phenoxy)titanium dichloride, dimethylsilyl(trimethylsilyl-cyclopentadienyl) (3-tert-butyl-2-phenoxy)titanium dichloride, dimethylsilyl(trimethylsilylcyclopentadienyl)-(3-tert-butyl-5-methyl-2-phenoxy)titanium dichloride, dimethylsilyl(trimethylsilylcyclopentadienyl)(3,5-di-tert-butyl-2-phenoxy)titanium dichloride, dimethylsilyl-(trimethylsilylcyclopentadienyl)(5-methyl-3-phenyl-2-phenoxy) titanium dichloride, dimethylsilyl(trimethylsilyl-cyclopentadienyl)(3-tert-butyl-dimethylsilyl-5-methyl-2-phenoxy)titanium dichloride, dimethylsilyl(trimethylsilyl-cyclopentadienyl)(5-methyl-3-trimethylsilyl-2-phenoxy)-titanium dichloride, dimethylsilyl(trimethylsilyl-cyclopentadienyl)(3-tert-butyl-5-methoxy-2-phenoxy) titanium dichloride, dimethylsilyl (trimethylsilylcyclopentadienyl)-(3-tert-butyl-5-chloro-2-phenoxy)titanium dichloride, dimethylsilyl (trimethylsilylcyclopentadienyl)(3,5-diamyl-2-phenoxy) titanium dichloride, dimethylsilyl(indenyl)(2-phenoxy)titanium dichloride, dimethylsilyl(indenyl)(3-methyl-2-phenoxy)-titanium dichloride, dimethylsilyl(indenyl)(3,5-dimethyl-2-phenoxy) dichloride, dimethylsilyl(indenyl)(3-tert-butyl-2-phenoxy)titanium dichloride, dimethylsilyl-(indenyl)(3-tert-butyl-5-methyl-2-phenoxy)titanium dichloride, dimethylsilyl(indenyl)(3,5-di-tert-butyl-2-phenoxy)titanium dichloride, dimethylsilyl(indenyl)(5-methyl-3-phenyl-2-phenoxy)titanium dichloride, dimethylsilyl(indenyl)(3-tert-butyldimethylsilyl-5-methyl-2-phenoxy)titanium dichloride, dimethylsilyl(indenyl)(5-methyl-3-trimethylsilyl-2-phenoxy)titanium dichloride, dimethylsilyl(indenyl)(3-tert-butyl-5-methoxy-2-phenoxy)-titanium dichloride, dimethylsilyl(indenyl)(3-tert-butyl-5-chloro-2-phenoxy)titanium dichloride, dimethylsilyl-(indenyl)(3,5-diamyl-2-phenoxy) titanium dichloride, dimethylsilyl(fluorenyl)(2-phenoxy)titanium dichloride, dimethylsilyl(fluorenyl)(3-methyl-2-phenoxy)-titanium dichloride, dimethylsilyl(fluorenyl)(3,5-dimethyl-2-phenoxy)titanium dichloride, dimethylsilyl(fluorenyl)(3-tert-butyl-2-phenoxy)titanium dichloride, dimethylsilyl-(fluorenyl)(3-tert-butyl-5-methyl-2-phenoxy)titanium dichloride, dimethylsilyl(fluorenyl)(3,5-di-tert-butyl-2-phenoxy)titanium dichloride, dimethylsilyl(fluorenyl)(5-methyl-3-phenyl-2-phenoxy)titanium dichloride, dimethylsilyl(fluorenyl) (3-tert-butyldimethylsilyl-5-methyl-2-phenoxy)titanium dichloride, dimethylsilyl-(fluorenyl)(5-methyl-3-trimethylsilyl-2-phenoxy)titanium dichloride, dimethylsilyl(fluorenyl)(3-tert-butyl-5-methoxy-2-phenoxy)titanium dichloride, dimethylsilyl-(fluorenyl)(3-tert-butyl-5-chloro-2-phenoxy) titanium dichloride, dimethylsilyl(fluorenyl)(3,5-diamyl-2-phenoxy)-titanium dichloride, dimethylsilyl(tetramethylcyclopentadienyl) (1-naphthox-2-yl)titanium chloride, the above compounds in which (cyclopentadienyl) is replaced by(dimethylcyclopentadienyl), (trimethylcyclopentadienyl), (ethylcyclopentadienyl), (n-propylcyclopentadienyl), (isopropylcyclopentadienyl), (sec-butylcyclopentadienyl), (isobutylcyclopentadienyl), (tert-butyldimethylsilyl-cyclopentadienyl), (phenylcyclopentadienyl), (methylindenyl) or (phenylindenyl), the above compounds in which 2-phenoxy is replaced by 3-phenyl-2-phenoxy, 3-trimethylsilyl-2-phenoxy or 3-tert-butyldimethylsilyl-2-phenoxy, the above compounds in which dimethylsilyl is replaced by diethylsilyl, diphenylsilyl or dimethoxysilyl, the above compounds in which titanium is replaced by zirconium or hafnium and the above compounds in which chloride is replaced by bromide or iodide.

Examples of the 1,3-diene compound (3) include butadiene, 1,3-pentadiene, isoprene, 1,3-hexadiene, 2,4-hexadiene, 2,3-dimethylbutadiene, 1,3-heptadiene, 2,4-heptadiene, 2,3-dimethyl-1,3-pentadiene, 1,3-octadiene, 2,4-octadiene, 3,5-octadiene, 3,4-dimethyl-2,4-hexadiene, 5,5-dimethyl-1,3-hexadiene, 2,2,7,7-tetramethyl-3,5-octadiene, 2,4,5,7-tetramethyl-3,5-octadiene, 1-phenyl-butadiene, 2-phenylbutadiene, 1,4-diphenylbutadiene and 2,3-diphenylbutadiene. Among them, butadiene, 2,4-hexadiene, 2,3-dimethylbutadiene and 1,4-diphenylbutadiene are preferable. A compound having a 1,3-diene structure has cis- and trans-isomers. The above compounds may be either one of the isomers or a mixture of the isomers.

The amount of the 1,3-diene compound (3) is usually from 1 to 10 moles per mole of the halogenated transition metal complex (2).

Examples of alkali metals or alkali metals in compounds include lithium, sodium and potassium. Examples of the alkali metal compounds include methyllithium, ethyllithium, n-propyllithium, n-butyllithium, sec-butyllithium, tert-butyllithium, lithium hydride and sodium hydride. Among them, n-butyllithium is preferable.

Examples of alkaline earth metals or alkaline earth metals in compounds include magnesium, calcium and barium. Examples of the alkaline earth metal compounds include methylmagnesium bromide, ethylmagnesium bromide, n-propylmagnesium bromide, isopropylmagnesium bromide, n-butylmagnesium bromide, sec-butylmagnesium bromide, methylmagnesium chloride, ethylmagnesium chloride, n-propylmagnesium chloride, isopropylmagnesium chloride, n-butylmagnesium chloride and sec-butylmagnesium chloride. Among them, isopropylmagnesium bromide and isopropyl-magnesium chloride are preferable.

The amount of the alkali metal or the alkali metal compound, or the alkaline earth metal or the alkaline earth metal compound to be used is usually from 1.5 to 3.0 moles, preferably from 1.8 to 2.2 moles, per one mole of the halogenated transition metal complex of the formula (2).

The method of adding the respective components in the present reaction includes the following methods: a method of adding the alkali metal or the alkali metal compound, or the alkaline earth metal or the alkaline earth metal compound to a mixture of the halogenated transition metal complex of the formula (2) and the 1,3-diene compound of the formula (3); or a method of adding the halogenated transition metal complex of the formula (2) to a mixture of the 1,3-diene compound of the formula (3) and the alkali metal or the alkali metal compound, or the alkaline earth metal or the alkaline earth metal compound. In this regard, the order of adding the components may be reverse to the above-described order.

The reaction is usually carried out in a solvent inert to the reaction. Examples of such a solvent are aprotic solvents which include aromatic hydrocarbon solvents such as benzene and toluene; aliphatic hydrocarbon solvents such as hexane and heptane; ether solvents such as diethyl ether, tetrahydrofuran and 1,4-dioxane; amide solvents such as hexamethylphosphoric amide and dimethylformamide; polar solvents such as acetonitrile, propionitrile, acetone, diethyl ketone, methyl isobutyl ketone and cyclohexanone; and halogen-containing solvents such as dichloromethane, dichloroethane, chlorobenzene and dichlorobenzene. These solvents may be used alone or as a mixture of two or more of them. The amount of the solvent is usually from 1 to 200 parts by weight, preferably from 3 to 50 parts by weight, per one part by weight of the halogenated transition metal complex of the formula (2).

While the reaction temperature is not limited in the present invention, the reaction is carried out at a temperature of preferably from higher than −100° C. to the boiling point of the solvent or lower, more preferably from −80 to 150° C.

The desirable transition metal complex (1) may be isolated from the resultant reaction mixture by any of the conventional methods, for example, a method comprising the steps of separating the formed precipitate by filtration and concentrating the filtrate to obtain the transition metal complex (1) by filtration.

[Catalyst for Olefin Polymerization]

The catalyst for olefin polymerization according to the present invention comprises the transition metal complex (1) as a catalytic component for polymerizing the olefin, and this catalyst can be prepared by bringing the transition metal complex (1) into contact with other co-catalytic component. An example of such a catalyst is a catalyst for olefin polymerization obtained by bringing the transition metal complex (1) into contact with a compound (A) and/or a compound (B) described below:

Compound (A): at least one aluminum compound selected from the group consisting of the following compounds (A1) to (A3):

(A1): an organoaluminum compound of the formula:

$$E^1_a AlZ_{(3-a)},$$

(A2): a cyclic aluminoxane having a structure of the formula: $\{-Al(E^2)-O-\}_b$, and (A3): a linear aluminoxane having a structure of the formula: $E^3\{-Al(E^3)-O-\}_c Al(E^3)_2$ wherein a is a number satisfying the equation of $0<a\leq 3$; b is an integer of 2 or more; c is an integer of 1 or more; each of $E^1$, $E^2$ and $E^3$ represents a $C_1$-$C_{20}$ hydrocarbon group, with the proviso that a plurality of $E^1$s, a plurality of $E^2$s and a plurality of $E^3$s may be the same or different from one another, respectively; and Z represents a hydrogen atom or a halogen atom, with the proviso that a plurality of Zs may be the same or different from one another; and Compound (B): at least one boron compound selected from the group consisting of the following boron compounds (B1) to (B3):

(B1): a boron compound of the formula: $BQ^1Q^2Q^3$, (B2): a boron compound of the formula: $G^+(BQ^1Q^2Q^3Q^4)^-$, and (B3): a boron compound of the formula:

$$(L^1\text{-}H)^+(BQ^1Q^2Q^3Q^4)^-$$

wherein B represents a trivalent boron atom; $Q^1$, $Q^2$, $Q^3$ and $Q^4$ represent independently of one another a halogen atom, a hydrocarbon group, a halogenated hydrocarbon group, a substituted silyl group, an alkoxy group or a disubstituted amino group; $G^+$ represents an inorganic or organic cation; and $L^1$ represents a neutral Lewis base.

Examples of the organoaluminum compound (A1) represented by the formula: $E^1_a AlZ_{(3-a)}$ include trialkyl-aluminums such as trimethylaluminum, triethylaluminum, tripropylaluminum, triisobutylaluminum and trihexylaluminum; dialkylaluminum chlorides such as dimethylaluminum chloride, diethylaluminum chloride, dipropylaluminum chloride, diisobutylaluminum chloride and dihexylaluminum chloride; alkylaluminum dichlorides such as methylaluminum dichloride, ethylaluminum dichloride, propylaluminum dichloride, isobutylaluminum dichloride and hexylaluminum dichloride; and dialkylaluminum hydride such as dimethylaluminum hydride, diethylaluminum hydride, dipropylaluminum hydride, diisobutylaluminum hydride and dihexylaluminum hydride. Among them, trialkylaluminums are preferable, and triethylaluminum and triisobutylaluminum are more preferable.

In the cyclic aluminoxane (A2) having the structure of $\{-Al(E^2)-O-\}_b$ or the linear aluminoxane (A3) having the structure of $E^3\{-Al(E^3)-O-\}_c Al(E^3)_2$, examples of $E^2$ and $E^3$ include alkyl groups such as a methyl group, an ethyl group, a n-propyl group, an isopropyl group, a n-butyl group, an isobutyl group, a n-pentyl group and a neopentyl group, b is an integer of 2 or more; and c is an integer of 1 or more. Preferably, $E^2$ and $E^3$ represent independently of one another a methyl group or an isobutyl group; b is an integer of 2 to 40; and c is an integer of 1 to 40.

The aluminoxanes described above are produced by various methods. While the preparation methods are not particularly limited, the aluminoxanes may be prepared by known methods. For example, the aluminoxane is prepared by bringing a solution of a trialkylaluminum (e.g., trimethyl-aluminum) in an appropriate organic solvent (e.g., benzene or an aliphatic hydrocarbon) into contact with water, or by bringing a trialkylaluminum (e.g., trimethylaluminum) into contact with a metal salt containing crystal water (e.g., coppersulfate hydrate).

In the boron compound (B1) of the formula: $BQ^1Q^2Q^3$, B represents a trivalent boron atom; $Q^1$ to $Q^3$ preferably represent independently of one another a halogen atom, a $C_1$-$C_{20}$ hydrocarbon group, a $C_1$-$C_{20}$ halogenated hydrocarbon group, a $C_1$-$C_{20}$ hydrocarbon-substituted silyl group, a $C_1$-$C_{20}$ alkoxy group or a $C_2$-$C_{20}$ hydrocarbon-disubstituted amino group, more preferably a halogen atom, a $C_1$-$C_{20}$ hydrocarbon group or a $C_1$-$C_{20}$ halogenated hydrocarbon group.

Specific examples of the boron compound represented by the formula: $BQ^1Q^2Q^3$ include tris(pentafluorophenyl)borane, tris(2,3,5,6-tetrafluorophenyl)borane, tris(2,3,4,5-tetrafluorophenyl)borane, tris(3,4,5-trifluorophenyl)borane and tris(2,3,4-trifluorophenyl)borane, phenylbis(pentafluorophenyl)borane. Among them, tris(pentafluorophenyl)borane is preferable.

In the boron compound (B2) of the formula: $G^+(BQ^1Q^2Q^3Q^4)^-$, $G^+$ represents an inorganic or organic cation; B represents a trivalent boron atom; and $Q^1$ to $Q^4$ are the same as defined above for $Q^1$ to $Q^3$ in the compound (B1).

In the boron compound (B2) of the formula: $G^+(BQ^1Q^2Q^3Q^4)^-$, examples of $G^+$ as the inorganic cation include a ferrocenium cation, an alkyl-substituted ferrocenium cation and a silver cation; and examples of $G^+$ as the organic cation include triphenylmethyl cation.

Examples of the moiety $(BQ^1Q^2Q^3Q^4)^-$ include tetrakis(pentafluorophenyl)borate, tetrakis(2,3,5,6-tetrafluoro-phenyl)borate, tetrakis(2,3,4,5-tetrafluorophenyl)borate, tetrakis(3,4,5-trifluorophenyl)borate, tetrakis(2,2,4-trifluorophenyl)borate, phenylbis(pentafluorophenyl)borate and tetrakis(3,5-bis-trifluoromethylphenyl)borate.

Examples of the boron compound (B2) represented by the formula: $G^+(BQ^1Q^2Q^3Q^4)^-$ include ferrocenium tetrakis(pentafluorophenyl)borate, 1,1'-dimethylferrocenium tetrakis(pentafluorophenyl)borate, silvertetrakis-(pentafluorophenyl)borate, triphenylmethyltetrakis-(pentafluorophenyl)borate and triphenylmethyltetrakis(3,5-bis-trifluoromethylphenyl)borate. Among them, triphenylmethyltetrakis(pentafluorophenyl)borate is preferable.

In the boron compound (B3) of the formula: $(L^1-H)^+(BQ^1Q^2Q^3Q^4)^-$, $L^1$ represents a neutral Lewis base; $(L^1-H)^+$ represents a Brønsted acid; B is a trivalent boron atom; and $Q^1$ to $Q^4$ are the same as defined above for $Q^1$ to $Q^3$ in the compound (B1).

In the boron compound (B3) of the formula: $(L^1-H)^+(BQ^1Q^2Q^3Q^4)^-$, examples of $(L^1-H)^+$ include trialkyl-substituted ammonium, N,N-dialkylanilinium, dialkylammonium and triarylphosphonium; and examples of $(BQ^1Q^2Q^3Q^4)^-$ are the same as defined above.

Examples of the boron compound (B3) represented by the formula: $(L^1-H)^+(B Q^1Q^2Q^3Q^4)^-$ include triethylammonium tetrakis(pentafluorophenyl)borate, tripropylammonium tetrakis(pentafluorophenyl)borate, tri(n-butyl)ammonium tetrakis(pentafluorophenyl)borate, tri(n-butyl)ammonium tetrakis(3,5-bis-trifluoromethylphenyl)borate, N,N-dimethylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-dimethylanilinium tetrakis(3,5-bis-trifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri(methylphenyl)phosphonium tetrakis(pentafluorophenyl)borate and tri(dimethylphenyl)phosphonium tetrakis(pentafluorophenyl)borate. Among them, tri(n-butyl)ammonium tetrakis(pentafluorophenyl)borate and N,N-dimethylanilinium tetrakis(pentafluoro-phenyl)borate are preferable.

As the compound (B), usually, any of the compound (B1) of the formula: $BQ^1Q^2Q^3$, the compound (B2) of the formula: $G^+(B Q^1Q^2Q^3Q^4)^-$ and the compound (B3) of the formula: $(L^1-H)^+(B Q^1Q^2Q^3Q^4)^-$ is used.

In the production of the catalyst for olefin polymerization, as the method of bringing the respective catalytic components into contact with one another, two catalytic components arbitrarily selected may be previously brought into contact with each other, and then, the remaining one catalytic component may be allowed to contact the former catalytic components; or the catalytic components may be brought into contact with one another in a polymerization reactor; or the catalytic components may be separately charged in an arbitral order into a polymerization reactor; or two or more catalytic components arbitrarily selected may be previously brought into contact with one another and then may be charged into a polymerization reactor.

The amounts of the respective catalytic components to be used are described below. The molar ratio of the compound (A) (in terms of an aluminum atom)/the transition metal complex (1) is usually from 0:1 to 10,000:1, preferably from 5:1 to 2,000:1. When the organoaluminum compound (A1) is used as the compound (A), the molar ratio of the compound (A) to the transition metal complex (1) is more preferably from 0:1 to 500:1, still more preferably from 0.5:1 to 100:1. The molar ratio of the compound (B) to the transition metal complex (1) is usually from 0.01:1 to 100:1, preferably from 0.5:1 to 10:1.

When the catalytic components are used in the form of a solution, the concentration of the transition metal complex (1) in the solution is usually from 0.0001 to 5 mmol/L, preferably from 0.001 to 1 mmol/L; the concentration of the compound (A) in terms of an aluminum atom is usually from 0.01 to 500 mmol/L, preferably from 0.1 to 100 mmol/L; and the concentration of the compound (B) is usually from 0.0001 to 5 mmol/L, preferably from 0.001 to 1 mmol/L.

[Production of Olefin Polymer]

In the polymerization process of the present invention, an olefin is polymerized in the presence of the catalyst for olefin polymerization which comprises the transition metal complex (1) as the catalytic component.

As the olefin to be polymerized, linear olefins and cyclic olefins are used; and a single olefin may be homopolymerized, or two or more olefins may be copolymerized. As the olefin, a $C_2$-$C_{20}$ olefin is usually used.

Examples of the linear olefins include α-olefins having 3 to 20 carbon atoms such as ethylene, propylene, 1-butene, 1-pentene, 1-hexene, 1-heptene, 1-octene, 1-nonene, 1-decene, 3-methyl-1-pentene, 4-methyl-1-pentene, 3,3-dimethyl-1-butene, 5-methyl-1-hexene and 3,3-dimethyl-1-pentene; non-conjugated dienes such as 1,5-hexadiene, 1,4-hexadiene, 1,4-pentadiene, 1,5-heptadiene, 1,6-heptadiene, 1,6-octadiene, 1,7-octadiene, 1,7-nonadiene, 1,8-nonadiene, 1,8-decadiene, 1,9-decadiene, 1,12-tetradecadiene, 1,13-tetradecadiene, 4-methyl-1,4-hexadiene, 5-methyl-1,4-hexadiene, 7-methyl-1,6-octadiene, 3-methyl-1,4-hexadiene, 3-methyl-1,5-hexadiene, 3-ethyl-1,4-hexadiene, 3-ethyl-1,5-hexadiene, 3,3-dimethyl-1,4-hexadiene and 3,3-dimethyl-1,5-hexadiene; and conjugated dienes such as 1,3-butadiene, isoprene, 1,3-hexadiene and 1,3-octadiene.

With regard to the cyclic olefins, examples of alicyclic olefins includes mono-olefins such as vinylcyclopentane, vinylcyclohexane, vinylcycloheptane, norbornene, 5-methyl-2-norbornene, 5-ethyl-2-norbornene, 5-butyl-2-norbornene, tetracyclododecene, tricyclodecene, tricyclo-undecene, pentacyclopentadecene, pentacyclohexadecene, 8-methyltetracyclododecene and 8-ethyltetracyclododecene; non-conjugated dienes such as 5-ethylidene-2-norbornene, dicyclopentadiene, 5-vinyl-2-norbornene, norbornadiene, 5-methylene-2-norbornene, 1,5-cyclooctadiene, 7-methyl-2,5-norbornadiene, 7-ethyl-2,5-norbornadiene, 7-propyl-2,5-norbornadiene, 7-butyl-2,5-norbornadiene, 7-pentyl-2,5-norbornadiene, 7-hexyl-2,5-norbornadiene, 7,7-dimethyl-2,5-norbornadiene, 7,7-methylethyl-2,5-norbornadiene, 7-chloro-2,5-norbornadiene, 7-bromo-2,5-norbornadiene, 7-fluoro-2,5-norbornadiene, 7,7-dichloro-2,5-norbornadiene, 1-methyl-2,5-norbornadiene, 1-ethyl-2,5-norbornadiene, 1-propyl-2,5-norbornadiene, 1-butyl-2,5-norbornadiene, 1-chloro-2,5-norbornadiene, 1-bromo-2,5-norbornadiene, 5,8-endomethylenehexahydronaphthalene and vinylcyclohexene; and conjugated dienes such as 1,3-cyclooctadiene and 1,3-cyclohexadiene. Examples of aromatic compounds include styrene, o-methylstyrene, m-methylstyrene, p-methylstyrene, o,p-dimethylstyrene, o-ethylstyrene, m-ethylstyrene, p-ethylstyrene, α-methylstyrene and divinylbenezene.

Examples of the combination of olefins for the copolymerization of olefins include combinations of linear olefins such as ethylene/propylene, ethylene/1-butene, ethylene/1-hexene, ethylene/propylene/1-butene, ethylene/propylene/1-hexene, propylene/1-butene and propylene/1-hexene; and combinations of linear olefin(s) and cyclic olefin(s) such as ethylene/vinylcyclohexane, ethylene/norbornene, ethylene/tetracyclododecene, ethylene/5-ethylidene-2-norbornene, propylene/vinyl-cyclohexane, propylene/norbornene, propylene/tetracyclododecene, propylene/5-ethylidene-2-norbornene, ethylene/propylene/5-ethylidene-2-norbornene.

While the polymerization method is not particularly limited, for example, there may be employed solution polymerization or slurry polymerization which uses a solvent such as an aliphatic hydrocarbon (e.g., butane, pentane, hexane, heptane and octane) or an aromatic hydrocarbon (e.g., benzene and toluene) or a halogenated hydrocarbon (e.g., methylene dichloride); or gas-phase polymerization carried out in gaseous monomers. These polymerization methods may be carried out continuously or batch-wise.

The polymerization temperature is usually from −50 to 300° C., preferably from −20 to 250° C., more preferably from 100 to 200° C. The polymerization pressure is preferably from an atmospheric pressure to 90 MPa. While the polymerization time is appropriately determined generally depending on the kind of an intended polymer and a reactor, it is preferably from one minute to 20 hours. In the present invention, a chain transfer agent such as hydrogen may be added in order to adjust the molecular weight of the polymer.

EXAMPLES

Hereinafter, the present invention will be described in more detail by way of Examples thereof, which do not limit the scope of the present invention in any way.

The physical properties of the polymer were measured by the following method.

(1) Proton Nuclear Magnetic Resonance Spectrum ($^1$H-NMR)

Apparatus: EX270 manufactured by JEOL LTD., or DPX-300 manufactured by Bruker

Sample cell: a 5 mmφ tube

Measuring Solvent: $CDCl_3$

Concentration of Sample: 10 mg/0.5 mL ($CDCl_3$)

Measuring Temperature: a room temperature (about 25° C.)

Measuring parameter: 5 mmφ probe, MENUF NON, OBNUC $^1$H; cumulated number: 16

Pulse Angle: 45°

Repeating time: ACQTM: 3 seconds, and PD: 4 seconds

Internal Standard: $CDCl_3$ (7.26 ppm)

Example 1

Synthesis of dimethylsilyl(2,3,4,5-tetramethylcyclopentadienyl) (3-tert-butyl-5-methyl-2-phenoxy)(1,4-diphenylbutadiene)titanium A mixture of dimethylsilyl(2,3,4,5-tetramethyl-cyclopentadienyl)(3-tert-butyl-5-methyl-2-phenoxy)titanium dichloride (1.38 g, 3.0 mmol), trans,trans-1,4-diphenyl-1,3-butadiene (0.62 g, 3.0 mmol) and hexane (150 mL) was cooled to −78° C., and a 1.6M solution (3.8 mL, 6.0 mmol) of n-butyl-lithium in hexane was added dropwise to the mixture. The resulting mixture was warmed to a room temperature and was then stirred for one hour, followed by refluxing for one hour. The insoluble materials were filtrated off, and the solvent was removed under a reduced pressure. The residue was recrystallized from hexane to obtain the entitled compound as a green solid (1.05 g; yield: 73%).

$^1$H-NMR ($CD_2Cl_2$, δ ppm) 0.25 (s, 6H, $SiMe_2$), 1.29 (s, 9H, t-Bu), 1.44 (s, 6H, $C_5Me_4$), 1.52 (s, 6H, $C_5Me_4$), 2.30 (s, 3H, Ar-Me), 4.40 (m, 2H, diene), 4.70 (m, 2H, diene), 6.60-7.50 (m, 12H, Ar—H).

Example 2

Synthesis of dimethylsilyl(2,3,4,5-tetramethylcyclopentadienyl) (3-tert-butyl-5-methyl-2-phenoxy)(2,5-hexadiene)titanium The operation of Example 1 was repeated except that 2,5-hexadiene (a mixture of isomers, 9.28 g, 9.0 mmol) was used instead of trans,trans-1,4-diphenyl-1,3-butadiene. As a result, the above-identified compound was obtained as a green solid (0.73 g; yield: 52%).

$^1$H-NMR ($CD_2Cl_2$, δ ppm): 0.51 (s, 6H, $SiMe_2$), 1.29 (s, 9H, t-Bu), 1.50 (s, 6H, $C_5Me_4$), 1.86 (s, 6H, $C_5Me_4$), 1.89 (d, J=5 Hz, 6H, $CH_3$—CH═CH—CH═CH—$CH_3$), 2.36 (s, 3H, Ar-Me), 2.48 (m, 2H, diene), 3.83 (m, 2H, diene), 6.96-6.97 (m, 2H, Ar—H), 7.03-7.04 (m, 2H, Ar—H).

Example 3

Synthesis of dimethylsilyl(2,3,4,5-tetramethylcyclopentadienyl) (3-tert-butyl-5-methyl-2-phenoxy)(2,3-dimethylbutadiene)titanium The operation of Example 1 was repeated except that 2,3-dimethyl-1,3-butadiene (9.28 g, 9.0 mmol) was used instead of trans,trans-1,4-diphenyl-1,3-butadiene. As a result, the above-identified compound was obtained as a purple solid (0.48 g; yield: 34%).

$^1$H-NMR ($CD_2Cl_2$, δ ppm): 0.48 (s, 6H, $SiMe_2$), 0.49 (d, J=9 Hz, 2H, CHH═CHMe-CHMe═CHH), 1.03 (s, 9H, t-Bu), 1.69 (s, 6H), 1.89 (s, 6H), 2.03 (s, 6H), 2.36 (s, 3H, Ar-Me), 2.77 (d, J=9 Hz, 2H, CHH═CHMe-CHMe═CHH), 6.97-7.03 (m, 2H, Ar—H), 7.07-7.13 (m, 2H, Ar—H).

<Production of Ethylene-α-Olefin Copolymer>

The physical properties of a copolymer were measured by the following methods.

(1) 1-Hexene Repeating Unit Content in Copolymer (SCB; unit: 1/1000 C)

An infrared spectrophotometer (EQUINOX55 manufactured by Bruker) was used to determine 1-hexene repeating unit content by infrared spectroscopy. As the characteristic absorption of butyl branches, a peak of 1,378 $cm^{-1}$ to 1,303 $cm^{-1}$ was used, and the 1-hexene repeating unit content was expressed as the number of butyl branches per 1,000 carbon atoms of an ethylene-1-hexene copolymer.

(2) Molecular Weight and Molecular Weight Distribution

The molecular weight of the copolymer was measured by gel permeation chromatography (GPC) under the following conditions. The molecular weight distribution was evaluated as a ratio of the weight average molecular weight (Mw) to the number average molecular weight (Mn), i.e., Mw/Mn.

Apparatus: a solution supplier (LC pump) Model 305 manufactured by Gilson (pump head: 25.SC)

Column: PLgel Mixed-B 10 μm (7.5 mmφ×300 mm) manufactured by PolymerLaboratories Measuring Temperature: 160° C.

Mobile Phase: o-Dichlorobenzene

Concentration of Sample: a copolymer (1 mg)/1,2,4-trichlorobenzene (1 mL)

Flow Rate: 2 mL/min.

Standard materials: (standard PS molecular weights) 5,000, 10,050, 28,500, 65,500, 185,400, 483,000, 1,013,000, 3,390,000

Ethylene and 1-hexene were copolymerized using each of the titanium complexes obtained in Examples 1 to 3 as a catalytic component for polymerizing an olefin and a 48-serial autoclave (PPR manufactured by Symyx), under the following polymerizing conditions described below.

Example 4

Toluene (5.0 mL) and 1-hexene (60 μL) were charged in an autoclave under a nitrogen atmosphere, and the mixture was stabilized at 40° C. After that, the autoclave was pressurized with ethylene up to 0.60 MPa, and the pressure of ethylene was stabilized. To the autoclave for polymerization, a solution of TIBA in hexane (40 μL) (TIBA concentration: 1.0 mol/L, manufactured by KANTO CHEMICAL), dimethylanilium tetrakis(pentafluorophenyl)borate (0.30 μmol) and the titanium complex (dimethylsilyl(2,3,4,5-tetramethylcyclo-pentadienyl)(3-tert-butyl-5-methyl-2-phenoxy)(1,4-diphenylbutadiene)titanium) (0.10 μmol) obtained in Example 1 were added. As a result of the polymerization, a polymer having the following properties was produced in an amount of $51.3 \times 10^6$ g per 1 mol of the catalyst and per one hour:
Molecular weight (Mw)=734,600; molecular weight distribution (Mw/Mn)=1.9; 1-hexene repeating unit content (SCB) in the copolymer=17.

Example 5

The polymerization was carried out in the same manner as in Example 4 except that the amount of 1-hexene was changed to 40 μL; the polymerization temperature was changed to 130° C.; and the amount of the solution of TIBA in hexane was changed to 4 μL. Thus, a polymer having the following properties was produced in an amount of $14.3 \times 10^6$ g per 1 mol of the catalyst and per one hour:
Molecular weight (Mw)=197,300; molecular weight distribution (Mw/Mn)=2.8; 1-hexene repeating unit content (SCB) in the copolymer=33.

Example 6

Toluene (5.0 mL) and 1-hexene (60 μL) were charged in an autoclave under a nitrogen atmosphere, and the temperature of the mixture was stabilized at 40° C. After that, the autoclave was pressurized with ethylene up to 0.60 MPa, and the pressure of ethylene was stabilized. To the autoclave for polymerization, a solution of TIBA in hexane (40 μL) (TIBA concentration: 1.0 mol/L, manufactured by KANTOU CHEMISTRY), dimethylanilium tetrakis(pentafluoro-phenyl)borate (0.30 μmol) and the titanium complex (dimethylsilyl(2,3,4,5-tetramethylcyclo-pentadienyl)(3-tert-butyl-5-methyl-2-phenoxy)(2,5-hexadiene)titanium) (0.10 μmol) obtained in Example 2 were added. As a result of the polymerization, a polymer having the following properties was produced in an amount of $43.6 \times 10^6$ g per 1 mol of the catalyst and per one hour:
Molecular weight (Mw)=759,700; molecular weight distribution (Mw/Mn)=1.9; 1-hexene repeating unit content (SCB) in the copolymer=16.

Example 7

The polymerization was carried out in the same manner as in Example 6 except that the amount of 1-hexene was changed to 40 μL; the polymerization temperature was changed to 130° C.; and the amount of the solution of TIBA in hexane was changed to 4 μL. Thus, a polymer having the following properties was produced in an amount of $40.9 \times 10^6$ g per 1 mol of the catalyst and per one hour:
Molecular weight (Mw)=245,000; molecular weight distribution (Mw/Mn)=2.9; 1-hexene repeating unit content (SCB) in the copolymer=23.

Example 8

Toluene (5.0 mL) and 1-hexene (60 mL) were charged in an autoclave under a nitrogen atmosphere, and the mixture was stabilized at 40° C. After that, the autoclave was pressurized with ethylene up to 0.60 MPa, and the pressure of ethylene was stabilized. To the autoclave for polymerization, a solution of TIBA in hexane (40 μL) (TIBA concentration: 1.0 mol/L, manufactured by KANTO CHEMICAL), dimethylanilium tetrakis(pentafluorophenyl)-borate (0.30 μmol) and the titanium complex (dimethylsilyl-(2,3,4,5-tetramethylcyclo-pentadienyl)(3-tert-butyl-5-methyl-2-phenoxy)(2,3-dimethylbutadiene)titanium) (0.10 μmol) obtained in Example 3 were added. As a result of the polymerization, a polymer having the following properties was produced in an amount of $32.1 \times 10^6$ g per 1 mol of the catalyst and per one hour:
Molecular weight (Mw)=801,800; molecular weight distribution (Mw/Mn)=1.9; 1-hexene repeating unit content (SCB) in the copolymer=17.

Example 9

The polymerization was carried in the same manner as in Example 8 except that the amount of 1-hexene was changed to 40 μL; the polymerization temperature was changed to 130° C.; and the amount of the solution of TIBA in hexane was changed to 4 μL. Thus, a polymer having the following properties was produced in an amount of $41.9 \times 10^6$ g per 1 mol of the catalyst and per one hour:
Molecular weight (Mw)=246,300; molecular weight distribution (Mw/Mn)=2.3; 1-hexene repeating unit content (SCB) in the copolymer=21.

Comparative Example 1

Toluene (5.0 mL) and 1-hexene (40 μL) were charged in an autoclave under a nitrogen atmosphere, and the mixture was stabilized at 130° C. After that, the autoclave was pressurized with ethylene up to 0.60 MPa, and the pressure of ethylene was stabilized. To the autoclave for polymerization, a solution of TIBA in hexane (40 μL) (TIBA concentration: 1.0 mol/L, manufactured by KANTO CHEMICAL), dimethylanilium tetrakis(pentafluorophenyl)borate (0.30 μmol) and (dimethylsilyl(2,3,4,5-tetramethyl-cyclopentadienyl)(3-tert-butyl-5-methyl-2-phenoxy)titanium dichloride) (0.10 μmol) were added. As a result of the polymerization, a polymer having the following properties was produced in an amount of $6.6 \times 10^6$ g per 1 mol of the catalyst and per one hour:
Molecular weight (Mw)=198,200; molecular weight distribution (Mw/Mn)=2.0; 1-hexene repeating unit content (SCB) in the copolymer=30.

To describe the present invention in still more detail, the X-ray diagram (ORTEP diagram) of dimethylsilyl(2,3,4,5-tetramethylcyclopentadienyl)(3-tert-butyl-5-methyl-2-phenoxy)(1,4-diphenylbutadiene)titanium obtained in Example 1 is shown below.

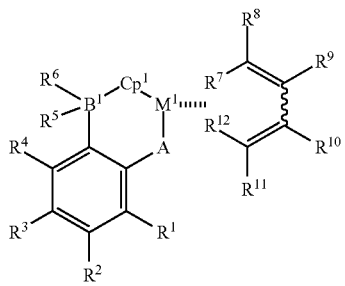

(1)

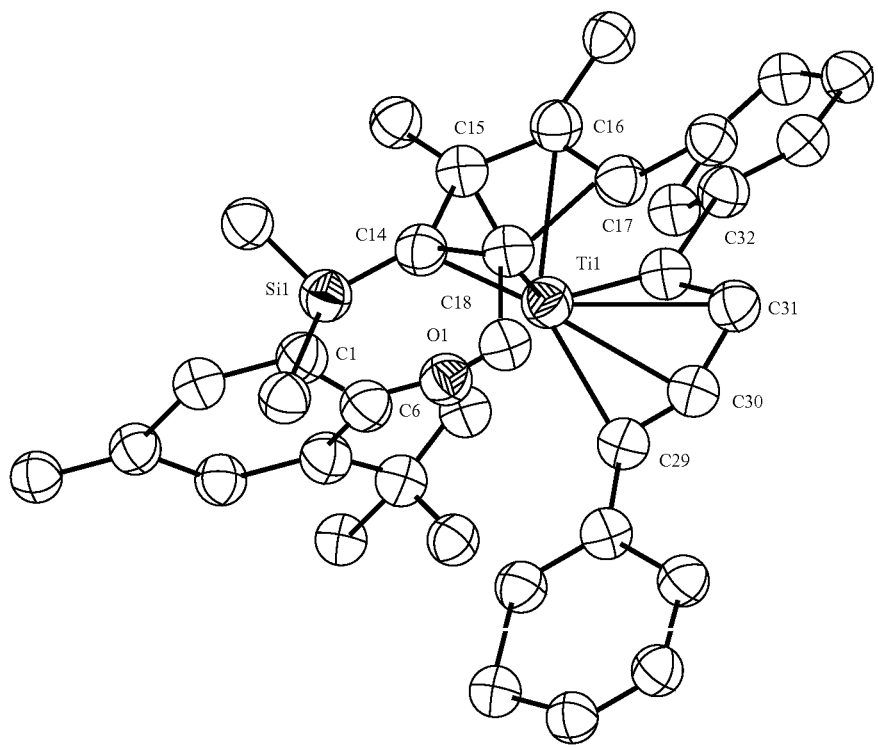

X-ray diagram (ORTEP diagram) of dimethylsilyl(2,3,4, tetramethylcyclopentadienyl)(3-tert-butyl-5-methyl-2-phenoxy)(1,4-diphenylbutadiene)titanium, wherein the notation of any hydrogen atom is omitted.

The invention claimed is:

1. A transition metal complex of the formula (1):

wherein A represents an atom of Group 16 of the periodic table;
$B^1$ represents an atom of Group 14 of the periodic table;
$M^1$ represents a transition metal atom of Group 4 of the periodic table;
$Cp^1$ represents a group having a cyclopentadiene anion backbone;
$R^1$, $R^2$, $R^3$, $R^4$, $R^5$ and $R^6$ represent independently of one another a hydrogen atom, a halogen atom, a $C_1$-$C_{20}$ alkyl group optionally substituted with a halogen atom, a $C_7$-$C_{20}$ aralkyl group optionally substituted with a halogen atom, a $C_6$-$C_{20}$ aryl group optionally substituted with a halogen atom, a $C_1$-$C_{20}$ hydrocarbon-substituted silyl group in which the hydrocarbon is optionally substituted with a halogen atom, a $C_1$-$C_{20}$ alkoxy group optionally substituted with a halogen atom, a $C_7$-$C_{20}$ aralkyloxy group optionally substituted with a halogen atom, a $C_6$-$C_{20}$ aryloxy group optionally substituted with a halogen atom, or a $C_2$-$C_{20}$ hydrocarbon-disubstituted amino group;

$R^7$, $R^8$, $R^9$, $R^{10}$, $R^{11}$, and $R^{12}$ represent independently of one another a hydrogen atom, a $C_1$-$C_{20}$ alkyl group optionally substituted with a halogen atom, a $C_7$-$C_{20}$ aralkyl group optionally substituted with a halogen atom, or a $C_6$-$C_{20}$ aryl group optionally substituted with a halogen atom, with the proviso that adjacent groups among $R^1$, $R^2$, $R^3$, $R^4$, $R^5$, $R^6$, $R^7$, $R^8$, $R^9$, $R^{10}$, $R^{11}$ and $R^{12}$ may be optionally bonded to each other to form a ring; and that a 1,3-diene consisting of $R^7$, $R^8$, $R^9$, $R^{10}$, $R^{11}$, $R^{12}$ and 4 carbon atoms coordinates on $M^1$ without any limitation of its coordination form, and the 1,3-diene may be of either a cis or trans form, or a mixed form thereof, and the double bonds may be delocalized.

2. The transition metal complex according to claim 1, wherein A is an oxygen atom.

3. The transition metal complex according to claim 1, wherein $B^1$ is a silicon atom.

4. The transition metal complex according to claim 1, wherein $M^1$ is a titanium atom.

5. The transition metal complex according to claim 1, wherein $R^7$ and $R^{12}$ are both hydrogen atoms.

6. The transition metal complex according to claim 1, wherein $R^8$ and $R^{11}$ are methyl groups or phenyl groups.

7. The transition metal complex according to claim 1, wherein $R^9$ and $R^{10}$ are methyl groups.

8. A process for producing the transition metal complex according to claim 1, characterized in that a halogenated transition metal complex of the formula (2) is reacted with a 1,3-diene compound of the formula (3) in the presence of an alkali metal or an alkali metal compound, or an alkaline earth metal or an alkaline earth metal compound:

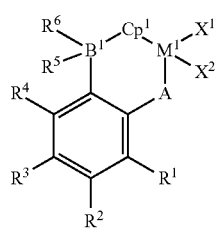
(2)

wherein A, $B^1$, $M^1$, $Cp^1$, $R^1$, $R^2$, $R^3$, $R^4$, $R^5$ and $R^6$ are the same as defined above; and $X^1$ and $X^2$ represent independently of one another a halogen atom); and

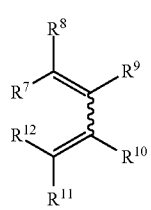
(3)

wherein $R^7$, $R^8$, $R^9$, $R^{10}$, $R^{11}$ and $R^{12}$ are the same as defined above; and the 1,3-diene structure may be of either a cis or trans form, or a mixed form thereof).

9. A catalytic component for olefin polymerization, which contains the transition metal complex according to claim 1.

10. A catalyst for use in polymerization of an olefin, obtained by bringing the catalytic component according to claim 9, into contact with the following compound (A) and/or the following compound (B), said compound (A) comprising at least one aluminum compound selected from the group consisting of the following compounds (A1) to (A3):

(A1): an organoaluminum compound of the formula:

$E^1_a AlZ_{(3-a)}$, (A2): a cyclic aluminoxane having a structure of the formula: $\{-Al(E^2)-O-\}_b$, and (A3): a linear aluminoxane having a structure of the formula: $E^3\{-Al(E^3)-O-\}_c Al(E^3)_2$ wherein a is a number satisfying the equation of $0 < a \leq 3$; b is an integer of 2 or more; c is an integer of 1 or more; each of $E^1$, $E^2$ and $E^3$ represents a $C_1$-$C_{20}$ hydrocarbon group, with the proviso that a plurality of $E^1$s, a plurality of $E^2$s and a plurality of $E^3$s may be the same or different from one another, respectively; and Z represents a hydrogen atom or a halogen atom, with the proviso that a plurality of Zs may be the same or different from one another; and Compound (B): one or more boron compounds selected from the group consisting of the following boron compounds (B1) to (B3):

(B1): a boron compound of the formula: $BQ^1Q^2Q^3$, (B2): a boron compound of the formula: $G^+(BQ^1Q^2Q^3Q^4)^-$, and (B3): a boron compound of the formula:

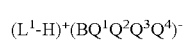
$(L^1-H)^+(BQ^1Q^2Q^3Q^4)^-$ wherein B represents a trivalent boron atom; $Q^1$, $Q^2$, $Q^3$ and $Q^4$ represent independently of one another a halogen atom, a hydrocarbon group, a halogenated hydrocarbon group, a substituted silyl group, an alkoxy group or a disubstituted amino group; $G^+$ represents an inorganic or organic cation; and $L^1$ represents a neutral Lewis base.

11. A process for producing an olefin polymer, characterized in that an olefin is polymerized in the presence of the catalyst according to claim 9.

12. A process for producing an ethylene-α-olefin copolymer characterized in that ethylene and an α-olefin are copolymerized in the presence of the catalyst according to claim 9.

13. A process for producing an ethylene-α-olefin copolymer, characterized in that an ethylene and an α-olefin are copolymerized at a temperature of 100° C or higher in the presence of the catalyst according to claim 9.

* * * * *